US011640755B2

(12) United States Patent
Beyer et al.

(10) Patent No.: US 11,640,755 B2
(45) Date of Patent: May 2, 2023

(54) REAL TIME DEFIBRILLATOR INCIDENT DATA

(71) Applicant: Avive Solutions, Inc., San Francisco, CA (US)

(72) Inventors: Rory M. Beyer, San Mateo, CA (US); Micah R. Bongberg, Kirkland, WA (US); Sameer Jafri, San Diego, CA (US); Gordon Moseley P. Andrews, Ross, CA (US)

(73) Assignee: Avive Solutions, Inc., Brisbane, CA (US)

( * ) Notice: Subject to any disclaimer, the term of this patent is extended or adjusted under 35 U.S.C. 154(b) by 0 days.

(21) Appl. No.: 17/539,909

(22) Filed: Dec. 1, 2021

(65) Prior Publication Data
US 2022/0092957 A1   Mar. 24, 2022

Related U.S. Application Data

(63) Continuation-in-part of application No. 17/155,852, filed on Jan. 22, 2021, now Pat. No. 11,210,919, which is a continuation-in-part of application No. 16/847,018, filed on Apr. 13, 2020, now Pat. No. 10,957,178, which is a continuation-in-part of
(Continued)

(51) Int. Cl.
*G08B 21/02* (2006.01)
*H04W 4/90* (2018.01)
*G08B 25/14* (2006.01)
*G08B 27/00* (2006.01)
*G08B 25/00* (2006.01)
*H04W 4/16* (2009.01)
(Continued)

(52) U.S. Cl.
CPC ........... *G08B 21/02* (2013.01); *G08B 25/006* (2013.01); *G08B 25/14* (2013.01); *G08B 27/001* (2013.01); *H04W 4/16* (2013.01); *H04W 4/90* (2018.02); *A61N 1/3904* (2017.08); *H04W 4/02* (2013.01)

(58) Field of Classification Search
CPC ..................................................... G08B 21/02
See application file for complete search history.

(56) References Cited

U.S. PATENT DOCUMENTS 6,292,687 B1   9/2001   Lowell et al.
6,356,785 B1   3/2002   Snyder et al.
(Continued)

FOREIGN PATENT DOCUMENTS

CN   105013085   11/2015
CN   108671401   10/2018
(Continued)

OTHER PUBLICATIONS

International Search Report and Written Opinion dated Apr. 22, 2021 from International Application No. PCT/US 21/14757.

*Primary Examiner* — Travis R Hunnings
(74) *Attorney, Agent, or Firm* — Beyer Law Group LLP

(57) ABSTRACT

System and methods for delivering defibrillator incident information to a PSAP in real-time during emergency use of an AED are described. Such information is utilized by a telecommunicator at a PSAP to provide better guidance to volunteer caregivers during potential cardiac arrest incidents. In another aspect the AED's current instruction state and optionally the time in that state is provided to the PSAP.

23 Claims, 7 Drawing Sheets

Related U.S. Application Data application No. 16/741,277, filed on Jan. 13, 2020, now Pat. No. 10,665,078, and a continuation-in-part of application No. 16/732,846, filed on Jan. 2, 2020, now Pat. No. 10,621,846, said application No. 16/741,277 is a continuation of application No. 16/562,870, filed on Sep. 6, 2019, now Pat. No. 10,580,280, said application No. 16/732,846 is a continuation of application No. 16/562,864, filed on Sep. 6, 2019, now Pat. No. 10,565,845.

(60) Provisional application No. 63/242,610, filed on Sep. 10, 2021, provisional application No. 63/081,166, filed on Sep. 21, 2020, provisional application No. 62/964,936, filed on Jan. 23, 2020, provisional application No. 62/846,346, filed on May 10, 2019, provisional application No. 62/731,306, filed on Sep. 14, 2018.

(51) Int. Cl.
  *H04W 4/02* (2018.01)
  *A61N 1/39* (2006.01)

(56) References Cited

U.S. PATENT DOCUMENTS

| | | |
|---|---|---|
| 6,493,581 B2 | 12/2002 | Russell |
| 6,658,290 B1 | 12/2003 | Lin et al. |
| 6,747,556 B2 | 6/2004 | Medema et al. |
| 6,834,207 B2 | 12/2004 | Miyauchi et al. |
| 6,937,150 B2 | 8/2005 | Medema et al. |
| 6,993,386 B2 | 1/2006 | Lin et al. |
| 7,289,029 B2 | 10/2007 | Medema et al. |
| 8,086,320 B2 | 12/2011 | Saketkhou |
| 8,180,457 B2 | 5/2012 | Matos |
| 8,209,008 B2 | 6/2012 | Hansen et al. |
| 8,565,871 B2 | 10/2013 | Tuysserkani |
| 8,706,225 B2 | 4/2014 | Matos |
| 8,818,522 B2 | 8/2014 | Mass et al. |
| 8,880,168 B2 | 11/2014 | Pearce et al. |
| 8,981,927 B2 | 3/2015 | McSheffrey |
| 9,026,147 B2 | 5/2015 | Galvin et al. |
| 9,035,787 B2 | 5/2015 | Bongberg et al. |
| 9,101,527 B2 | 8/2015 | Madanat |
| 9,232,040 B2 | 1/2016 | Barash et al. |
| 9,289,621 B2 | 3/2016 | Aoyama et al. |
| 9,295,849 B2 | 3/2016 | Elghazzawi et al. |
| 9,307,383 B1 | 4/2016 | Patrick |
| 9,324,120 B2 | 4/2016 | Braun |
| 9,480,852 B2 | 11/2016 | Bonnamy |
| 9,498,152 B2 | 11/2016 | Bowers |
| 9,592,401 B2 | 3/2017 | Freeman et al. |
| 9,619,767 B2 | 4/2017 | Braun |
| 9,628,946 B2 | 4/2017 | Elghazzawi |
| 9,847,030 B2 | 12/2017 | Kadobayashi et al. |
| 9,848,058 B2 | 12/2017 | Johnson et al. |
| 9,872,998 B2 | 1/2018 | Aoyama et al. |
| 9,889,311 B2 | 2/2018 | Horseman et al. |
| 9,897,459 B2 | 2/2018 | Johnson |
| 9,987,193 B2 | 5/2018 | Freeman |
| 10,035,023 B2 | 7/2018 | Das |
| 10,058,469 B2 | 8/2018 | Freeman |
| 10,058,709 B2 | 8/2018 | Tilton, Jr. |
| 10,090,716 B2 | 10/2018 | Stever et al. |
| 10,092,767 B1 | 10/2018 | Newton et al. |
| 10,099,061 B2 | 10/2018 | Buchanan |
| 10,159,848 B2 | 12/2018 | Amann et al. |
| 10,178,534 B2 | 1/2019 | Barash et al. |
| 10,298,072 B2 | 5/2019 | Stever et al. |
| 10,381,118 B2 | 8/2019 | Kellum |
| 10,449,380 B2 | 10/2019 | Andrews |
| 10,504,622 B2 | 12/2019 | Gallopyn et al. |
| 10,543,379 B2 | 1/2020 | Hingston et al. |
| 10,565,845 B1 | 2/2020 | Beyer et al. |
| 10,580,280 B1 | 3/2020 | Picco et al. |
| 10,621,846 B1 | 4/2020 | Beyer et al. |
| 10,638,929 B2 | 5/2020 | Kaib et al. |
| 10,657,796 B2 | 5/2020 | Bowers |
| 10,665,078 B1 | 5/2020 | Picco et al. |
| 10,744,063 B2 | 8/2020 | Freeman |
| 10,792,506 B2 | 10/2020 | Elghazzawi |
| 10,796,396 B2 | 10/2020 | Braun et al. |
| 10,806,939 B1 | 10/2020 | Malott et al. |
| 10,857,371 B2 | 12/2020 | Gustavson et al. |
| 10,861,310 B2 | 12/2020 | Picco et al. |
| 10,946,209 B2 | 3/2021 | Andrews et al. |
| 10,957,178 B2 | 3/2021 | Beyer et al. |
| 11,210,919 B2 * | 12/2021 | Beyer ............... G08B 25/006 |
| 2003/0149759 A1 | 8/2003 | Hetherington et al. |
| 2004/0015191 A1 | 1/2004 | Otman et al. |
| 2004/0049233 A1 | 3/2004 | Edwards |
| 2004/0064342 A1 | 4/2004 | Browne et al. |
| 2006/0030891 A1 | 2/2006 | Saltzstein et al. |
| 2006/0041278 A1 | 2/2006 | Cohen et al. |
| 2006/0149321 A1 | 7/2006 | Merry et al. |
| 2006/0149322 A1 | 7/2006 | Merry et al. |
| 2006/0149323 A1 | 7/2006 | Merry et al. |
| 2007/0032830 A1 | 2/2007 | Bowers |
| 2007/0136099 A1 | 6/2007 | Neligh et al. |
| 2007/0162075 A1 | 7/2007 | O'hara |
| 2007/0270909 A1 | 11/2007 | Saketkhou |
| 2007/0299473 A1 * | 12/2007 | Matos ............... A61N 1/3904 607/9 |
| 2008/0250166 A1 | 10/2008 | Edwards |
| 2009/0070148 A1 | 3/2009 | Skocic |
| 2009/0149894 A1 | 6/2009 | Merry et al. |
| 2009/0284348 A1 * | 11/2009 | Pfeffer ............... G08B 25/016 340/7.3 |
| 2009/0284378 A1 * | 11/2009 | Ferren ............... G08B 21/06 340/573.1 |
| 2010/0017471 A1 | 1/2010 | Brown et al. |
| 2010/0286490 A1 * | 11/2010 | Koverzin ............... G10L 17/26 704/231 |
| 2011/0060378 A1 | 3/2011 | Tuysserkani |
| 2011/0071880 A1 * | 3/2011 | Spector ............... H04W 76/50 340/539.13 |
| 2011/0117878 A1 | 5/2011 | Barash et al. |
| 2011/0152702 A1 * | 6/2011 | Goto ............... G16H 40/67 340/7.58 |
| 2012/0232355 A1 | 9/2012 | Freeman |
| 2012/0271370 A1 | 10/2012 | Hochhalter et al. |
| 2013/0012151 A1 | 1/2013 | Hankins |
| 2013/0065628 A1 | 3/2013 | Pfeffer |
| 2013/0296719 A1 | 11/2013 | Packer et al. |
| 2014/0002241 A1 | 1/2014 | Elghazzawi |
| 2014/0004814 A1 | 1/2014 | Elghazzawi |
| 2014/0031884 A1 | 1/2014 | Elghazzawi |
| 2014/0222096 A1 | 8/2014 | Hu et al. |
| 2014/0222466 A1 | 8/2014 | Kellum |
| 2014/0266718 A1 * | 9/2014 | Bongberg ............ A61N 1/3904 340/540 |
| 2015/0206408 A1 * | 7/2015 | LaLonde ............... A61B 5/349 340/539.12 |
| 2015/0343229 A1 * | 12/2015 | Peterson ............... G16Z 99/00 607/6 |
| 2016/0066653 A1 | 3/2016 | Piva et al. |
| 2016/0133160 A1 | 5/2016 | Packer et al. |
| 2016/0140834 A1 * | 5/2016 | Tran ............... A43B 3/42 340/539.11 |
| 2016/0148495 A1 | 5/2016 | Buchanan |
| 2016/0210581 A1 | 7/2016 | Braun |
| 2016/0213942 A1 | 7/2016 | Elghazzawi et al. |
| 2016/0217691 A1 * | 7/2016 | Kadobayashi ......... G16H 40/20 |
| 2016/0328950 A1 | 11/2016 | Pelletier et al. |
| 2017/0028211 A1 | 2/2017 | Tilton, Jr. |
| 2017/0172424 A1 | 6/2017 | Eggers et al. |
| 2017/0251347 A1 | 8/2017 | Mehta et al. |
| 2017/0281016 A1 | 10/2017 | Elghazzawi |
| 2017/0281461 A1 | 10/2017 | Kokubo et al. |
| 2017/0289350 A1 | 10/2017 | Philbin |
| 2017/0367927 A1 | 12/2017 | Cervantes |

(56) References Cited

U.S. PATENT DOCUMENTS

| | | |
|---|---|---|
| 2018/0169426 A1 | 6/2018 | Montague et al. |
| 2018/0369598 A1 | 12/2018 | Newton et al. |
| 2019/0038133 A1 | 2/2019 | Tran |
| 2019/0044362 A1 | 2/2019 | Beyer et al. |
| 2019/0099608 A1 | 4/2019 | Elghazzawi et al. |
| 2019/0117983 A1 | 4/2019 | Andrews et al. |
| 2019/0117984 A1 | 4/2019 | Andrews et al. |
| 2019/0117987 A1 | 4/2019 | Beyer et al. |
| 2019/0117988 A1 | 4/2019 | Beyer et al. |
| 2019/0159009 A1 | 5/2019 | Barash et al. |
| 2019/0168010 A1 | 6/2019 | Elghazzawi |
| 2019/0174289 A1 | 6/2019 | Martin et al. |
| 2019/0279327 A1 | 9/2019 | Braun et al. |
| 2019/0306664 A1 | 10/2019 | Mehta et al. |
| 2019/0318827 A1 * | 10/2019 | Chiu .................. H04L 67/52 |
| 2020/0054885 A1 | 2/2020 | Aprile |
| 2020/0090483 A1 | 3/2020 | Picco et al. |
| 2020/0092700 A1 | 3/2020 | Picco et al. |
| 2020/0206517 A1 | 7/2020 | Martin et al. |
| 2020/0221263 A1 | 7/2020 | Sturman et al. |
| 2020/0242907 A1 | 7/2020 | Beyer et al. |
| 2020/0286352 A1 | 9/2020 | Beyer et al. |
| 2020/0286353 A1 | 9/2020 | Jafri et al. |
| 2020/0373005 A1 | 11/2020 | Halsne et al. |
| 2021/0142639 A1 | 5/2021 | Beyer et al. |
| 2021/0153817 A1 | 5/2021 | Beyer et al. |
| 2021/0154487 A1 | 5/2021 | Bongberg et al. |
| 2021/0228893 A1 | 7/2021 | Akram |
| 2021/0357456 A1 | 11/2021 | Hale et al. |
| 2021/0407273 A1 | 12/2021 | Jafri et al. |

FOREIGN PATENT DOCUMENTS

| | | |
|---|---|---|
| CN | 111539866 | 8/2020 |
| DE | 202004002106 | 6/2004 |
| EP | 1157717 | 1/2005 |
| EP | 2218478 | 8/2010 |
| EP | 2879759 | 10/2019 |
| JP | 2001/325689 | 11/2001 |
| JP | 2015-58030 | 3/2015 |
| KR | 20160012239 | 2/2016 |
| KR | 101780214 | 10/2017 |
| KR | 102152282 | 9/2020 |
| WO | 2010/66014 | 6/2010 |
| WO | 2018/069383 | 4/2018 |

* cited by examiner

REAL TIME DEFIBRILLATOR INCIDENT DATA

CROSS-REFERENCE TO RELATED APPLICATIONS

This application is a Continuation-in-Part of U.S. patent application Ser. No. 17/155,852, (P021) filed on Jan. 22, 2021. This application also claims priority of U.S. Provisional Patent Application No. 63/242,610 (P025P) filed on Sep. 10, 2021. Each of these applications is incorporated by reference in its entirety.

U.S. patent application Ser. No. 17/155,852 claims priority of U.S. Provisional Patent Application Nos.: 62/964,936, (P021P) filed on Jan. 23, 2020 and 63/081,166, (P021P2) filed on Sep. 21, 2020, both of which are incorporated by reference herein in their entirety.

In addition, U.S. patent application Ser. No. 17/155,852 is a Continuation-in-Part of U.S. patent application Ser. No. 16/847,018, (P014X1) filed on Apr. 13, 2020 (now U.S. Pat. No. 10,957,178, issued on Mar. 23, 2021), which is a Continuation-in-Part of U.S. patent application Ser. No. 16/732,846 (P014AC1) filed Jan. 2, 2020 (now U.S. Pat. No. 10,621,846, issued Apr. 14, 2020), which is a Continuation of U.S. patent application Ser. No. 16/562,864 (P014A) filed Sep. 6, 2019 (now U.S. Pat. No. 10,565,845, issued Feb. 18, 2020). U.S. patent application Ser. No. 16/847,018 is also a Continuation-in-Part of U.S. patent application Ser. No. 16/741,277 (P014BC1) filed Jan. 13, 2020 (now U.S. Pat. No. 10,665,078, issued May 26, 2020), which is a Continuation of U.S. patent application Ser. No. 16/562,870 (P014B) filed Sep. 6, 2019 (now U.S. Pat. No. 10,580,280, issued Mar. 3, 2020). Both U.S. patent application Ser. Nos. 16/562,864 and 16/562,870 claim the priority of U.S. Provisional Patent Application Nos.: 62/731,306 (P014P) filed Sep. 14, 2018, and 62/846,346 (P014P2) filed May 10, 2019. All of the foregoing applications are incorporated herein by reference in their entirety.

FIELD

The present disclosure relates generally to communicating defibrillator incident information to emergency call centers and many of the inventions described herein are particularly applicable to automated external defibrillators (AEDs).

BACKGROUND

Sudden cardiac arrest (SCA) is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed so that they can be used by a lay person in situations where professional medical help is not available.

Given their potential to save lives, automated external defibrillators have been deployed in a relatively wide variety of public and private locations so that they are available in the event that a person in the vicinity goes in to cardiac arrest. By way of example, AEDs may be found in corporate and government offices, shopping centers, airports, airplanes, restaurants, casinos, hotels, sports stadiums, schools, fitness centers and a variety of other locations where people may congregate.

Although the availability of AEDs has increased over the years, their relatively high cost tends to limit their placement and many locations including homes, workplaces, schools, sports fields, and a plethora of other places where people reside, frequent, or congregate don't have an on-site AED available. Furthermore, although many AEDs are considered "portable," most commercially available portable automated external defibrillators are bulky and heavy enough that they are rarely carried by people other than trained medical personnel. Thus, there are many times, locations and events where no AED is available when a cardiac arrest incident occurs. Even when an AED is nearby when a sudden cardiac arrest incident occurs, the AED is often not used because either its presence is unknown, or the device seems intimidating to bystanders who are reluctant to try to use a device that they are unfamiliar with to treat a medical situation that they are unfamiliar with.

When a cardiac arrest incident is witnessed, bystanders will typically call a known emergency number such as 911 in the U.S. and Canada, 112 in Europe, 999 in many jurisdictions, etc. Such calls go to emergency call centers which are sometimes referred to as Public Safety Answering Points (PSAPs) and include centers such as 911 call centers in the U.S. and Canada, 112 call centers in Europe, 999 call centers in various jurisdictions and other such emergency services call centers. When a call is received by an emergency call center, a call-taker (telecommunicator) typically speaks to the caller to try to determine/categorize the nature of the incident, its location, and the appropriate responders (e.g., police, fire, EMS, etc.) to handle the incident. Next, a dispatcher (who may also be the call-taker, depending on the jurisdiction) uses this information to assign emergency responders to the emergency.

Today, there is a clear movement within emergency response networks to try to get telecommunicators more actively involved in encouraging/directing bystanders to serve as caregivers that render aid to patients suffering from medical emergencies before emergency medical services (EMS) arrives. For cardiac arrest specifically, EMS Chiefs and Medical Directors are implementing telephone/telecommunicator CPR (T-CPR). That is, when a telecommunicator, in partnership with the caller, identifies a patient suffering from cardiac arrest, the telecommunicator will provide AED use and/or CPR instructions to the caller, as appropriate, in addition to quickly dispatching the appropriate EMS response. The belief is that the telecommunicator and the caller form a unique team in which the expertise of the telecommunicator and the willingness of the caller or a responder in proximity to the caller to provide CPR represents an opportunity to improve SCA survival rates. The American Heart Association provides T-CPR recommendations and guidance. See, e.g., https://cpr.heart.org/en/resuscitation-science/telephone-cpr/t-cpr-recommendations-and-performance-measures.

Although T-CPR is clearly helpful in some cases, it has limitations. One limitation is that the telecommunicator typically doesn't have the ability to independently monitor the volunteer responder's/caregiver's actions and is typically limited to feedback provided by the caller (which may or may not be the person actually performing CPR and/or using an AED). Therefore, it is sometimes difficult for the telecommunicator to determine whether any actions are being performed or evaluate the impact of actions being performed and provide effective instructions based on such evaluation.

A number of entities have proposed enabling two way voice communications between an AED and a telecommunicator at a PSAP or other call center. Similarly, a number of entities have proposed sending a message and/or selected defibrillator information to a PSAP when an AED is activated or in use. Although such proposals have been made, the challenges of implementing such systems are significant and the present inventors are unaware of any commercially available AEDs that actually support such functionality.

Although existing sudden cardiac arrest response systems have saved many lives, sudden cardiac arrest remains one of the leading causes of death. Accordingly, continuing efforts to develop systems that have the potential to improve cardiac arrest survival rates in different settings.

SUMMARY

To achieve the foregoing and other objects, methods, systems, AED network servers, emergency services interfaces and frameworks are described that facilitate delivering defibrillator incident information to a PSAP in real-time during emergency use of a defibrillator. Such information can be utilized by a telecommunicator at the PSAP to provide better guidance to volunteer caregivers and/or callers during a potential cardiac arrest incident.

In one aspect, selected defibrillator incident information generated by an AED is sent directly or indirectly to from the AED to an AED network server in real time during emergency use of the AED. The AED network server also receives the current location of the AED that has been deployed for emergency use. The AED network server then transmits the selected defibrillator incident information directly or indirectly to a Public Safety Answering Point (PSAP) responsible for handling calls to emergency services originating from an area that includes the current location of the AED. The defibrillator incident information is forwarded to the PSAP in real time during the emergency use of the AED thereby enabling the telecommunicator to provide more focused directions to a caregiver utilizing the AED or a caller at the location of the AED during the emergency use of the AED.

The AED network server may simply forward the defibrillator information as received, or it may process some of the received information before forwarding it to the PSAP in a format that is better suited for use at the PSAP.

Preferably, at least some of the defibrillator incident information is rendered on a display at the PSAP for use by the telecommunicator in real time while communicating with the caregiver or caller (e.g., to provide directions to the caregiver or caller during the emergency use of the AED based at least in part on the received information).

In some embodiments, the AED network server is responsible for determining the appropriate PSAP to forward the incident information to based at least in part on the current location of the AED. In others, the AED network server forwards the incident information to an emergency services interface which determines the appropriate PSAP to forward the incident information to based at least in part on the current location of the AED. In various embodiments, the PSAP integration functions of the AED network server and the emergency services interface may be consolidated at a single location—which can be at the location of an AED management server, at the location of a traditional emergency services interface or any other suitable location.

In various embodiments, the defibrillator incident information may be transmitted to the AED network server by any of: (a) a communications unit that is an integral part of the defibrillator; (b) an interface unit that is a separate unit that detachably attached to the defibrillator; (c) a communication unit associated with the defibrillator that is not physically attached to the defibrillator; (d) a mobile communication device having a defibrillator support app installed thereon that coordinates communications with the defibrillator and with the defibrillator network server; or (e) any other suitable mechanism.

In some embodiments, the selected defibrillator incident information includes a current instruction state of the AED. The defibrillator incident information may also include an indication of an amount of time that the AED has been in the current instruction state.

More generally, in some implementations, the defibrillator incident information conveyed to the PSAP may include one or more of: (i) a current instruction state of the AED; (ii) an indication of an amount of time that the AED has been in the current instruction state; (iii) a next instruction; (iv) a current operational state of the AED; (v) an indication of an amount of time that the AED has been in the current operational state; (vi) a shockable rhythm/non-shockable rhythm diagnosis made by the AED; (vii) a shock history associated with the incident; (viii) details of one or more shock(s) delivered by the AED; (ix) a timestamp that indicates when the AED was activated; (x) an indication of an amount of time that has passed since the AED was activated; (xi) an impedance detected by the AED or (xii) information indicative of a quality of CPR being administered by the caregiver; (xiii) an electrode pad status; (xiv) an indication of whether electrode pads associated with the AED have been removed from a pad storage location; (xv) an indication of whether the electrode pads are currently attached to a patient; (xvi) an indication of whether the electrodes pads have been previously attached to the patient but are no longer attached; (xvii) an indication of a language that the AED is currently providing instruction in; (xviii) an indication of a current ambient temperature; (xix) an AED self-test result or status; (xx) an AED serial number; (xxi) an electrode pad serial number; (xxi) a hardware and/or software version of the AED.

In some embodiments defibrillator incident information includes an impedance graph or feed that shows variations in the patient impedance as a function of time. Alternatively, or additionally, the incident information may include an ECG segment or ECG feed, a video feed or other streamed defibrillator sensor data.

In some embodiments, the system is configured so that the telecommunicator may send a message or alert to the AED via the AED network server—e.g., during emergency use of the AED. In some embodiments, the message sent to the AED is a triggering message that causes the AED to generate a predetermined audio instruction that is prestored by the AED. The triggering message may cause the AED to generate a variety of different instructions as may be appropriate based on the situation as understood by the telecommunicator.

In other aspects, specific types of defibrillator incident information are conveyed in real time from an AED to a PSAP. Such real time defibrillator incident information can be used by telecommunicator at a PSAP to provide better guidance to a caregiver utilizing the AED or a caller in close proximity to the caregiver. In some specific embodiments, a current instruction state of the AED is transmitted to the PSAP. In some embodiments, the defibrillator incident information also includes an indication of an amount of time that the AED has been in the current instruction state.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

Figure 1A:
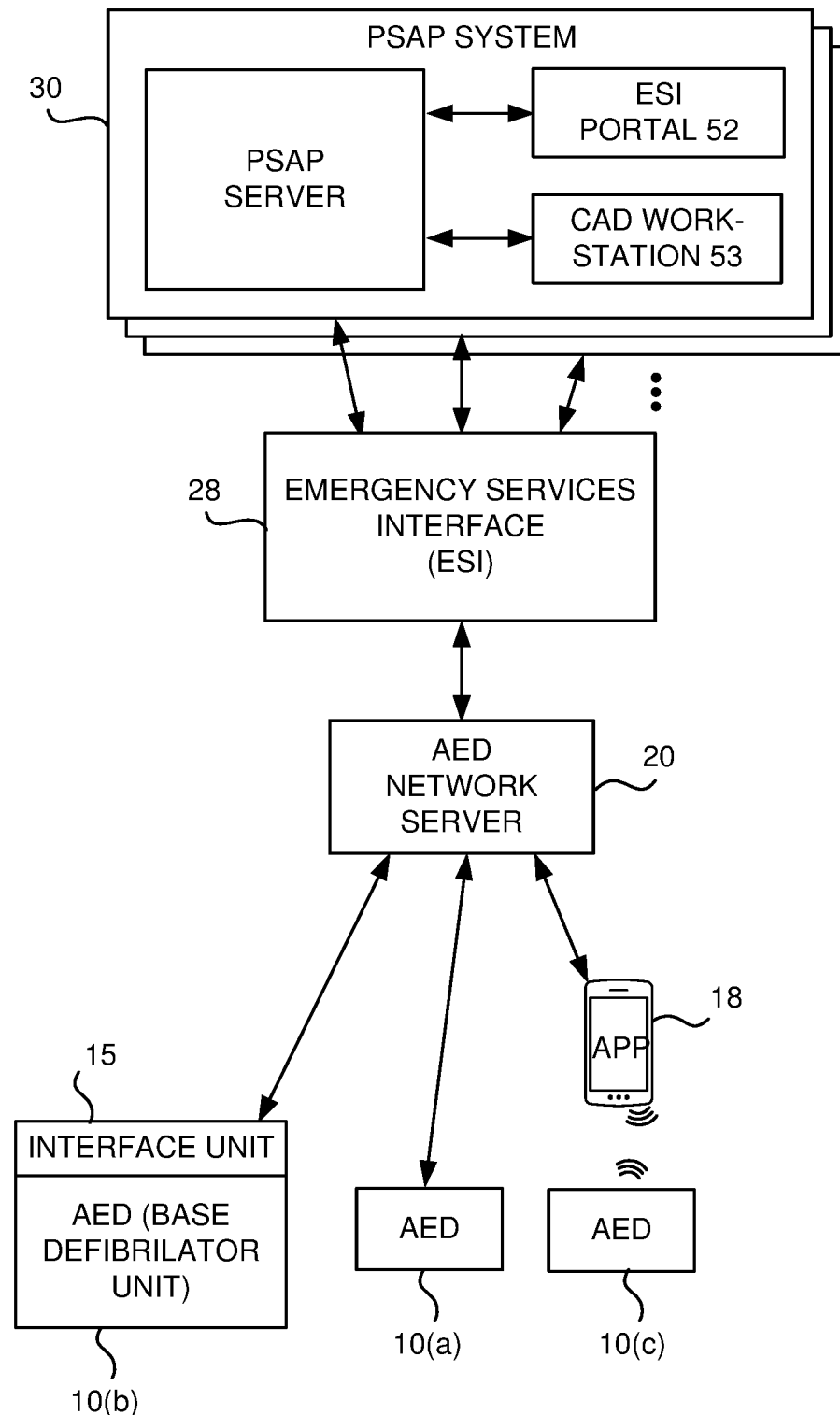
FIGS. 1A and 1B are block diagrams illustrating representative architectures for facilitating communications between an AED and a PSAP in accordance with two different embodiments.

An issue with T-CPR (which as used herein encompasses AED use guidance), and more generally with guidance provided by dispatchers/telecommunicators to volunteer responders/caregivers using an AED is that the telecommunicator often has little or no view of what is actually happening at the emergency scene and therefore doesn't have a way to determine whether their CPR and/or AED use instructions are at all effective. The present disclosure proposes sending selected defibrillator data and/or other incident data to the telecommunicator during use of the AED which may provide the telecommunicator with some level of feedback on the incident. With such information at hand, the telecommunicator can deliver more targeted and effective feedback for the AED user/volunteer responder that is trying to save a life.

In some implementations, such information is sent to the call center's Computer Aided Dispatch (CAD) System. In others, it may be sent to an emergency services interface (ESI) portal or an AED network portal acting as an ESI. In each of these cases, the defibrillator/incident data may be displayed on a display screen viewable by the telecommunicator (often referred to as the telecommunicator or dispatcher dashboard). For example, some call center workstations include both a CAD screen driven by the CAD system and a separate outside data screen driven by an emergency service interface (ESI) client designed to operate with one or more emergency services interfaces. In such systems, the defibrillator incident information may be presented through the ESI client. When a CAD system has the ability to integrate outside data into the CAD display, then the data may be shown directly on the CAD display. Of course, there are a variety of other pathways through which the defibrillator incident information can presented to the telecommunicator.

The information presented to the call center telecommunicator may vary with the preferences of different call center administrators and/or the entity that implements the integration, and the types of information that are actually available from the AED. For example, the information presented to the telecommunicator in real time may include information such as the current state of an AED being used on the victim, including whether or not the AED has been powered on; an indication of the AED state and/or an audio instruction state of the AED (i.e., what audio instruction is currently being communicated by the AED); how long the user has been on a specific AED state or on a specific instruction; the next expected instruction state; whether electrode pads have been removed from the AED (for application to the patient); whether the electrode pads are currently placed on a patient; whether the pads have previously been connected to a patient (when they are not currently connected to the patient); the time since the AED was activated; an operating mode of the AED (e.g., whether the AED is in child (pediatric) or adult mode); an operational language (e.g., English/Spanish, etc.); a timestamp that indicates when the AED was activated or an indication of the amount of time that has passed since the AED was activated; the patient's impedance—which may be one or more discrete measurements, a graph, or continuous (streamed); changes to the patient's impedance; ECG samples or streamed ECG data; an available classification of the latest cardiac rhythm detected by the AED (which may be a simple shockable/not shockable classification, or if/when available, a more specific classification of the detected rhythm); the detected ECG waveform; indications of whether a shock has been delivered; the nature of a or each delivered shock(s) (e.g., energy level delivered, the time the shock was delivered, etc.); the number of shocks delivered; CPR compression depth, CPR rate, CPR recoil; a feed of streamed defibrillator sensor data; a Serial Number, hardware version and/or software version of the AED; an electrode pad Serial Number and Status (e.g., expired, used or good); an ambient temperature (which may be useful to the dispatcher for instructing the user to move if possible); a "self-test status" which indicates whether the AED passed its self-tests; an AED battery charge level; the geo-coordinates of the AED; and/or a variety of other information as desired by the call center.

The information available to the telecommunicator may also include information about AEDs that are near an incident. This can be helpful in the scenario where an AED is not immediately at hand at the scene of a potential cardiac arrest incident as a bystander may be instructed to go get an AED. Such information may include the specific location of nearby AEDs (e.g., the geo-coordinates and/or street address, etc. of the AED), and when desired, selected operational status information about such AEDs (e.g., operational status, self-test results status, battery charge level, etc.). This can be helpful in that it facilitates the PSAP dispatcher guiding a caller to a nearby AED. In some applications, the PSAP dispatcher/telecommunicator also has the ability to activate a volunteer/AED responder network as described in U.S. Pat. Nos. 10,621,846 and 10,665,078 or to select volunteer responders from a list presented on the dispatcher's dashboard. The referenced patent applications are incorporated herein by reference. In such circumstances, the information available to the telecommunicator may further include the location, path of travel, etc. of such responders and/or AEDs.

When available from the defibrillator or a device associated therewith, other real time information can be provided as well. For example, if CPR compression rate or compression depth feedback is available from the defibrillator or an associated device, such feedback can also be provided to the telecommunicator. Similarly, if the defibrillator or a device associated therewith supports audio or video communication, an audio and/or video feed may be delivered to the telecommunicator and/or two way communications may be supported through the defibrillator or the associated device.

The defibrillator state information (and particularly the emergency workflow state of the defibrillator) can be particularly useful because it gives the telecommunicator insight as to where the user is in the emergency workflow and thereby allows the telecommunicator to better tailor their advice and instructions to the immediate situation. The indication of how long the user has been on a particular instruction can be helpful since it may indicate that the user is having difficulty with a particular step and the telecommunicator can tailor their advice/instructions to that step. For example, if the AED has been stuck on a "Place Electrode Pads" instruction for an extended time, the telecommunicator knows to intervene and potentially help the user through that step. In another example, when the telecommunicator knows that next step that is coming, they can prepare the user to act accordingly.

The detected patient impedance can be used for several purposes. For example, if the impedance indicates an open circuit, that may suggest that at least one of the electrode pads has not yet been properly placed on the patient's body and the telecommunicator's instructions can be tailored appropriately. When the measured impedance is reported to be in an expected range, that suggests that the pads have been placed properly which may be confirmed by the caller or vice versa. If the measured impedance is outside of an expected range, that may suggest that the pads have been placed improperly and the telecommunicator can tailor their guidance accordingly.

In some embodiments, a real-time feed of the patient impedance, or the patient's ECG, as sensed by the AED electrode pads is provided to the call center and is displayed on the telecommunicator's CAD system. Patient impedance and/or ECG can be helpful because, when CPR is being administered, the detected patient impedance and ECG is expected to vary in a discernible manner with factors such as chest compressions. Thus, a real-time impedance or ECG log can be used to confirm that the responder/caregiver is indeed trying to perform CPR and can provide some level of feedback on the nature of the CPR being performed. The real-time impedance or ECG measurements are a very valuable piece of information as they can give the telecommunicator some indication as to whether the user is performing CPR, and whether CPR is being applied at the right time. For example, with many AEDs, CPR is not supposed to be performed when the AED is analyzing the heart rhythm for classification purposes. When both the patient impedance (or ECG) and the current AED state are provided, the dispatcher can verify that the caregiver is performing CPR when intended and importantly is not continuing with the CPR in periods when the AED is in an "analyzing heart rhythm" state or preparing to deliver a defibrillation shock (stand_back) state. The real-time detected impedance can also be a helpful indicator of whether the caregiver (or other bystander) is touching the patient during an inappropriate period (e.g., when analyzing the patient's heart rhythm, during shock delivery, etc.). Real-time impedance or ECGs can be provided in feeds that stream current data that is rendered in graphs at the PSAP, or discrete graphs transmitted to the PSAP in frequent intervals to provide updates.

Information such as the specific location of nearby AEDs (e.g., geo-coordinates) and whether any of these AEDs have been powered-on can be helpful because it gives the telecommunicator an idea of whether there is an AED at the scene, nearby the scene, or on its way to the scene. In practice there are times when an AED is already present or readily available at the scene of a sudden cardiac incident when EMS arrives, but it was never used simply because the bystanders didn't feel confident enough to try to use the AED. By providing the telecommunicator with a mechanism for knowing that an AED is at or nearby the scene but has not yet been activated, the telecommunicator can encourage the caller to use the AED (e.g., there is an AED on scene, turn it on and I'll guide you through using it). In another example, as will be described in more detail below, when a responder/bystander picks up a connected AED in response to an incident alert, the AED may frequently or continuously convey its location to the call center. This allows the telecommunicator to see the AED traveling to the victim in real-time. In still another example the telecommunicator can direct a caller to the location of a nearby AED.

Some AEDs and/or AED accessories are designed to detect chest compressions. Some detect the rate of chest compressions, others detect the depth of compressions, and some detect both. Some CPR detectors are accelerometer based, others utilize electrocardiograms or impedance cardiograms, and others contemplate using other types of sensors. Regardless of the type of CPR detectors used, when available, the information made available by such devices may additionally or alternatively be provided to the telecommunicator. Of course, any other information that is available from the defibrillator may also or alternatively be provided to the telecommunicator's CAD system for use by the telecommunicator.

There are a number of different workflows by which an AED may be associated with a particular emergency (e.g., 911) call. In some instances, a bystander may call 911 (or other appropriate emergency call center). The dispatcher may diagnose the incident as a potential cardiac arrest incident and activate a responder network. A responder may accept the emergency alert through an AED, which associates the AED with the particular incident. When an emergency alert is accepted through an AED or an AED is otherwise deployed, it begins sending real-time incident data to the dispatcher so that the dispatcher has increased visibility as to what is actually happening at the emergency scene before EMS arrives.

In other instances, an AED or a communications unit associated therewith may be configured to automatically contact an emergency call center (PSAP) when the AED is deployed. As will be described in more detail below, the PSAP may be contacted through an AED network server or other suitable intermediary(ies). The AED or a device associated with the AED may further be configured to provide its geo-location to the call center. Separately, a bystander may have already called or may subsequently call 911. When the call center receives a bystander call, the call taker will verify the incident location if it has already been entered automatically in the CAD system or determine and enter the incident location (if it has not already been entered automatically). The CAD system, an ESI portal or other suitable system may be configured to automatically determine when an AED activation appears to coincide with an incident location associated with a voice call and flag the co-location to the telecommunicator. The telecommunicator can then confirm with the caller that the AED is present at the incident location and is being used on the patient. Alternatively, the telecommunicator may manually check to see whether there is an activated AED that appears to coincide with the incident location. If so, the telecommunicator may make the association themself. In still other circumstances, voice communications may be supported on the same channel that delivers the defibrillator data which directly ties the data and voice call. Regardless of the way that the association is made, at this point, the telecommunicator understands that the incident and the incident data from the AED relate to the same event and can act accordingly.

FIG. 1A illustrates a communication architecture in accordance with a first embodiment that is suitable for facilitating the aforementioned communications from an AED (or a communications unit associated with an AED) to a PSAP. The architecture includes a subject AED 10 (represented as AEDs 10(a), 10(b) and 10(c), an AED network server 20, an emergency services interface (ESI) 28 and the participating PSAP 30. In some embodiments, an intermediary device is used to facilitate communications between the AED and the AED network servers. A variety of different types of devices can be used as intermediaries, with some of the most likely including: an interface unit 15 mounted on and at least semi-permanently attached to the AED; a nearby mobile communications device 18 (e.g., a Smartphone) executing an app configured to communicate with the AED; and/or a communications unit (not shown) that is associated with, but not necessarily attached to the AED.

Some AEDs (e.g., 10(a) in FIG. 1) have built-in cellular and/or Wi-Fi communication abilities and have the ability to communicate directly with the AED network server 20 through a cellular or Wi-Fi/Internet network. Others may be configured to communicate with the AED network server through an intermediary device. For example, Applicant has described a modular defibrillator architecture in which an interface unit 15 may optionally be mounted on and detachably attached to a base defibrillator unit (e.g., AED 10(b) in FIG. 1). In some such embodiments, the base defibrillator unit is a fully functional AED. When the base defibrillator unit is activated for emergency use with the interface unit 15 attached thereto, the base defibrillator unit periodically sends status messages to the interface unit 15 that provide information about defibrillator's then current status. The interface unit passes such messages on to the AED network server 20 as appropriate. By way of example, such an architecture is described in U.S. Pat. Nos. 10,773,091 and 10,737,105, which are incorporated herein by reference.

In other instances, a mobile communication device 18 or other suitable communications units may serve as the intermediary between the AED (e.g., AED 10(c) in FIG. 1) and the network server 20. A number of communications protocols have been proposed for conveying defibrillator information to a server through an intermediary. For example, Applicant has described an architecture in which an AED broadcast status messages wirelessly using a short range communications protocol such as Bluetooth Low Energy (BLE). The wireless messages can be received by any of a variety of listening devices, including cell phones, and other suitable listening devices (including, when desired, interface unit 15). When the listener has an app or other software or firmware designed to receive and process such broadcasts, the receiving listener can forward the received messages on to the AED network server 20 as appropriate. Such a communications architecture is described in U.S. patent application Ser. Nos. 16/733,591 and 16/733,684, which are incorporated herein by reference. Additionally, or alternatively, a wireless connection may be established between the AED and the intermediary device to facilitate the transfer of defibrillator information to the intermediary device. In still other embodiments, the mobile communications device 18 or other suitable listener may communicate with the AED through a wired connection such as a USB-C cable.

The AED network server 20 may be a server that has the ability to communicate with (or at least receive communications from) a number of different AEDs either directly or indirectly through appropriate intermediaries. In various implementations, the AED network server 20 may optionally also serve as an AED management server that helps coordinate management of the various AEDs, and/or as an AED responder network server that facilitates sending incident alerts to AEDs and/or volunteer responders as described in U.S. Pat. Nos. U.S. Pat. Nos. 10,621,846 and 10,665,078, which are incorporated herein by reference.

The AED network server 20 is configured to communicate with an emergency services interface (ESI) 28. By way of background PSAPs were originally designed to handle voice calls (e.g., 911 calls), but were not well suited to receive data from external sources that might be relevant to such calls. As the availability of data relevant to emergency incidents increased, emergency services interfaces were developed that helped route data (including, but not limited to device data) that is relevant to a particular incident to the correct PSAP and to provide mechanisms for associating such data with the correct voice call(s) reporting an incident. In general, ESIs have the ability to receive data relevant to an emergency incident, determine the appropriate PSAP to handle that incident based on the location of the incident, and deliver the relevant data to the appropriate PSAP in a manner than can be utilized by a telecommunicator that is handling a voice call.

Telecommunicators within a PSAP will frequently have access to an ESI portal that allows them to receive data relevant to various emergency calls. This may take the form of a separate ESI screen, an ESI frame or window within the computer aided dispatch (CAD) system or in other suitable presentations. In such systems, the telecommunicator is able to view data associated with a voice call in the ESI portal. In some circumstances, the ESI serves as a clearinghouse for data supplied to the PSAP. That is, the ESI may take data from one or more distinct sources, process such data appropriately and display the relevant information on the telecommunicator's ESI portal.

In the United States, RapidSOS is currently the largest emergency services interface and is well suited for such applications. One particularly desirable feature of RapidSOS is that they currently have relationships with a large percentage of the emergency call centers in the United States and are already set up to send data received from other sources, including data from other connected devices (not defibrillators) to the call centers. Although RapidSOS is mentioned specifically, it should be appreciated that the same approach can be used with any or with multiple different ESIs as appropriate.

The ESI 28 is configured communicate with a number of (and potentially a large number of) PSAPs 30. The ESI can use the location data forwarded by the AED network server to determine the appropriate PSAP 30 to handle any particular incident. As discussed above, the PSAP's CAD system or an ESI portal 52 which may be associated with the CAD system is designed to receive data relating to incidents from the ESI 28.

Figure 1B:
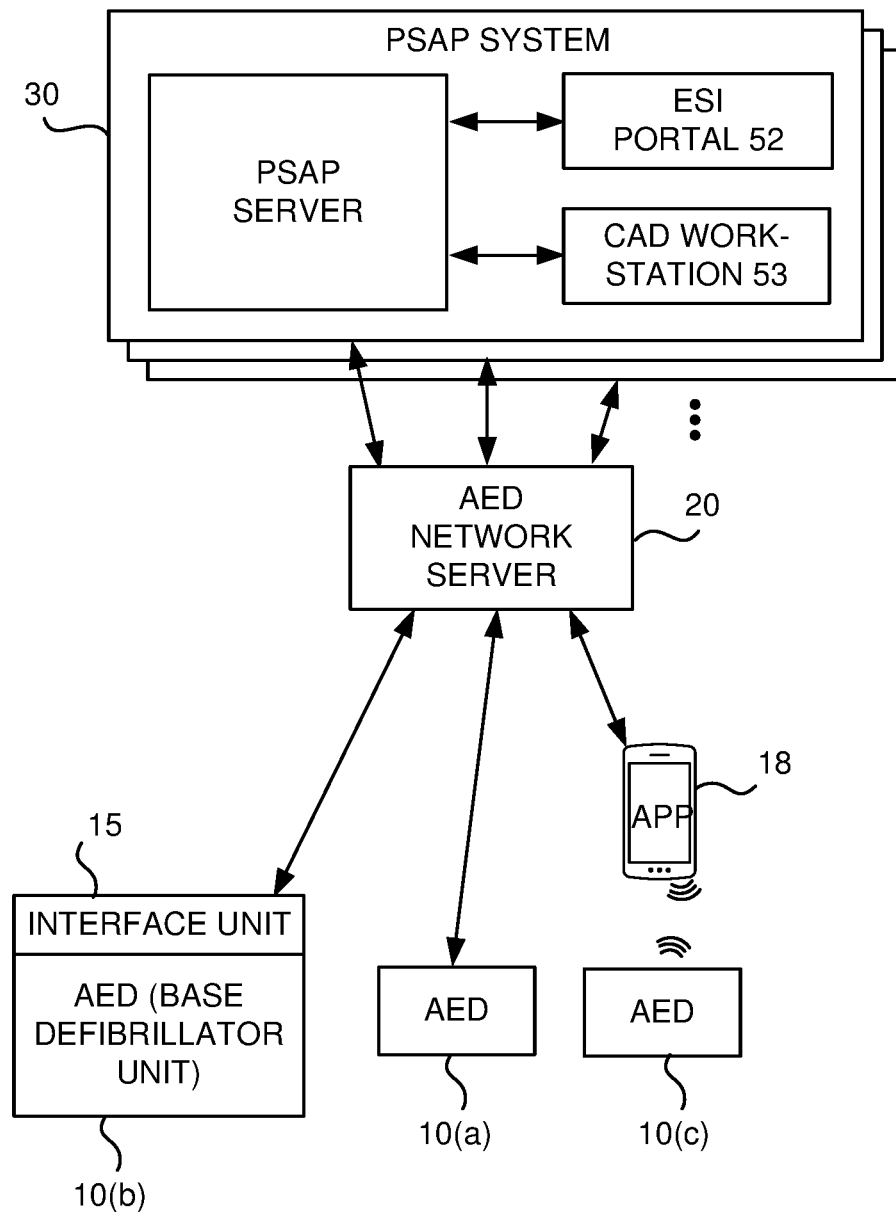

In some embodiments, the functionality of the ESI 28 may be integrated into the AED network server 20 (or vice versa). Such an architecture is illustrated in FIG. 1B which is substantially similar to the architecture discussed above with respect to FIG. 1A except that the AED Network server 20 itself determines the appropriate PSAP for any particular incident based on the incident location reported by the AED (and any other relevant factors). The AED network server then communicates directly with the selected PSAP thereby eliminating the need for a separate ESI.

In some circumstances the AED network server 20 also functions as an AED management server. That is, it is responsible for non-emergency management of the AEDs. In such circumstances, it may receive regular status reports from the AEDs when the AEDs are in standby mode and may send notifications to the AEDs owners/administrators when maintenance is required (e.g., the AED battery needs to be charged or replaced, the electrode pads need to be replaced, etc.). The AED management server may handle a wide variety of functions including software updates and providing owners with the ability to manage AEDs that they are responsible for.

In other embodiments, the AED network server may only be responsible for handling emergency communications with the AEDs or only handling communications between AEDs and PSAPs during emergency use of the AEDs. That is, the AED network server 20 is effectively an AED emergency network server and a separate AED management server is provided for non-emergency communications or for any non-PSAP related communications. A potential advantage of the integrated approach is that the AED (or a communications unit associated with the AED) only needs to communicate with one designated server regardless of whether it is in an emergency operating mode or a standby mode. Additionally, since there will often be substantial overlap between the handling of emergency and non-emergency messages, it may reduce the need for maintaining parallel systems with many duplicate functions. Conversely, a potential advantage of discrete emergency and non-emergency network servers is that network bandwidth taken up by non-emergency communication can't adversely impact the emergency AED network server.

In some implementations the AED network server may also function as a responder network server as described in U.S. patent application Ser. No. 16/847,018, which is incorporated herein by reference.

Figure 2A:
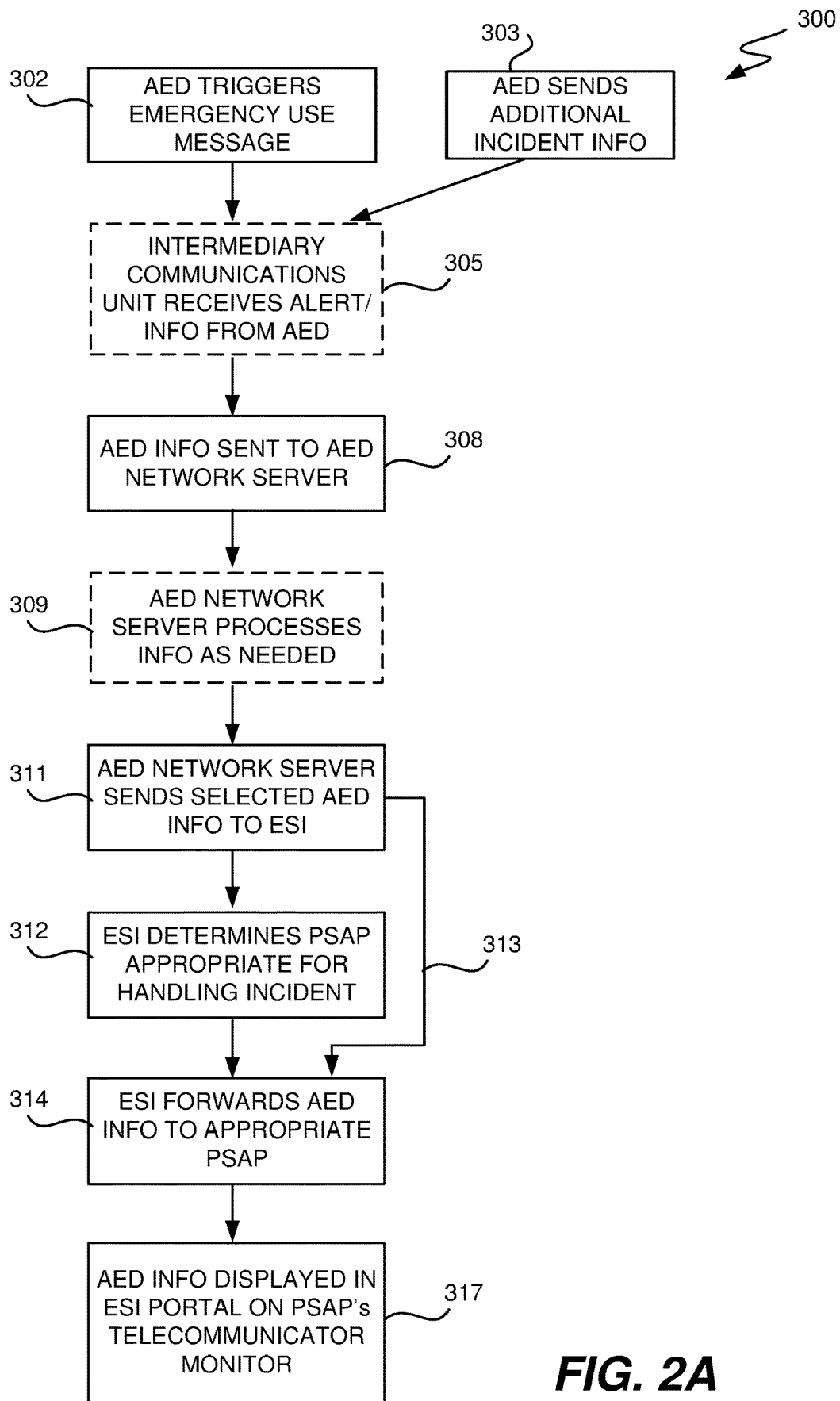
FIGS. 2A and 2B are flow charts illustrating representative communications between an AED and a PSAP in accordance with two different embodiments corresponding to the two different embodiments illustrated in FIGS. 1A and 1B.

FIG. 2A is a flow chart that illustrates a communications path/protocol 300 for transmitting defibrillator related information from an AED (or an intermediary device associated with an AED) to an appropriate PSAP for use by a telecommunicator at the PSAP. In some circumstances, the receiving telecommunicator may be handling a live voice call with the caregiver using the AED or another responsible bystander. In such circumstances, the defibrillator information received at the PSAP can be used to help support T-CPR. Independently, if/when the desired/permitted within the context of the PSAP's dispatch protocols, the defibrillator information can potentially be used as a trigger for dispatching emergency medical services (EMS) to the scene of the incident when the information provided to the PSAP includes the geo-location of the AED that is in use.

In some embodiments, an initial emergency use message or alert 302 is generated when the AED is activated for use in an emergency setting. The initial emergency use alert may be discrete message that is sent when the AED is used in an emergency, or it may be inferred from the contents of a status message or status report that is more routinely sent by the defibrillator. In practice, a variety of different triggers may be used to initiate such a message. In some embodiments, the initial emergency use alert 302 is generated when the AED is first activated (e.g., when a power button is activated), or the electrode pads are opened or removed from their storage location, or an electrode pad cartridge is opened, etc. In others, the emergency use alert may be generated when the AED detects an impedance suggestive that the electrode pads have been placed on a patient. In still others, the emergency use alert 302 may be generated when the AED is first turned on in a non-training mode. Of course, other triggers can be used as well.

When such an initial emergency use alert is triggered, the AED, or a communications unit associated with the AED transmits selected information to a server that the AED (or a communications unit associated with the AED) is configured to communicate with as represented by block 308 (e.g., AED network server 20). In some implementations, the AED network server may be a server that performs various AED management services in addition to handling messages from the AED or communication unit in the emergency use setting now described.

As discussed above, in some implementations, the AED may be configured to communicate directly with the AED network server 28 (e.g., through a cellular or Wi-Fi/Internet network). In others, the AED may communicate through an intermediary such as, an interface unit 15 attached to the AED, a nearby mobile communications device 18 (e.g. a Smartphone) or another external communications unit that is associated with the AED. The use of such an intermediary is illustrated by optional block 305 in FIG. 2A. When an intermediary is used, the initial use alert is transmitted from the AED to the intermediary 305 and then from the intermediary to the AED network server 308. Alternatively, in some embodiments, the intermediary device may be configured to independently detect the activation/use of the AED.

Applicant has described systems that routinely send status messages to either (or both of) an attached interface unit or other intermediary devices such as nearby mobile phones both when the AED is in an emergency mode and when the AED is in the standby mode. Such status messages can be sent over wired or wireless communications paths and effectively accomplish step 305. The receiving intermediary devices are configured to automatically forward the status reports to an AED network server 28 together with the geo-location of the intermediary thereby effectively accomplishing step 308. When appropriate, the intermediary can forward additional information as well.

The status messages sent during emergency use of the AED may contain a variety of information that may be useful to a telecommunicator. By way of example, such information may include, a unique incident identifier, an indication of whether the AED has been activated, the current AED state (which may include a current instruction state), an indication of whether the electrode pads have been deployed, the impedance detected by the pads, the nature of any cardiac rhythms detected by the AED, any of the other AED information discussed above or below, etc. If the AED is location aware, it can include its current location. Alternatively, when available, the location may be supplied by the intermediary device (e.g., the interface unit 15, mobile communications device 18, etc.).

When the AED network server 20 first receives a message indicating that an AED has been deployed and is being used in an emergency setting, the AED network server 20 sends an incident alert to the ESI server 28 as represented by block 311. In practice this may take the form of an API call or any other suitable message format. The incident alert includes incident information received by the AED network server that is considered relevant to the telecommunicator and an indication of the location of the incident (e.g., geo-location). It may also include information that has been processed or summarized by the AED network server 20.

The ESI 28 uses the incident location identified in the incident alert to determine the PSAP that is appropriate for handling calls from the geographic area that includes the location of the incident as represented by block 312. The ESI then establishes a data connection with the appropriate PSAP and delivers the defibrillator incident information/data to that PSAP as represented by block 314. Alternatively, if the ESI has a standing connection with the target PSAP, the incident information may be delivered over that standing connection. The defibrillator data is then displayed on the screen of the telecommunicator handling the incident as represented by block 317 (e.g., on a CAD workstation 53 display or ESI portal 52).

At this point, there are connections or at least established communications paths between each of the nodes in the delivery path. The AED network server may have a connection established with either an intermediary device (e.g., interface unit 15, smartphone 18, etc.) or the AED 10(*a*) itself. The AED network server 20 also has a direct connection with the ESI 28. The ESI server 28, in turn has a direct connection with the PSAP. With these connections in place, any further updates provided by the AED can be immediately transmitted to the PSAP, thereby providing a path for delivering real-time defibrillator incident data from the AED to the appropriate PSAP and for continually updating such data in real time. Block 303 in FIG. 2A illustrates the transmission of such additional information. The additional information may then be conveyed to the appropriate PSAP following the same path. The telecommunicator at the PSAP that is responsible for handling the incident can use the information received to help facilitate the incident response. That can include helping the dispatcher guide a user (e.g., to facilitate T-CPR), determining the resources needed for the incident, passing information to EMS, and a variety of other suitable uses.

To help the various nodes associate messages with a particular incident, each message preferably includes a unique incident identifier. The incident identifier provides each receiving node with a mechanism for correlating later received information with an earlier reported incident. A variety of techniques can be used to assign the unique incident identifier to a particular incident and the incident identifier may take a variety of forms. By way of example, in one specific implementation, a unique number that can be used as the incident identifier may be formed from otherwise useful information by concatenating the AED's serial number and the time that the AED was activated. Of course, the incident identifiers may be selected in a variety of other ways and in some implementations the incident identifier may be a UUID.

Figure 2B:
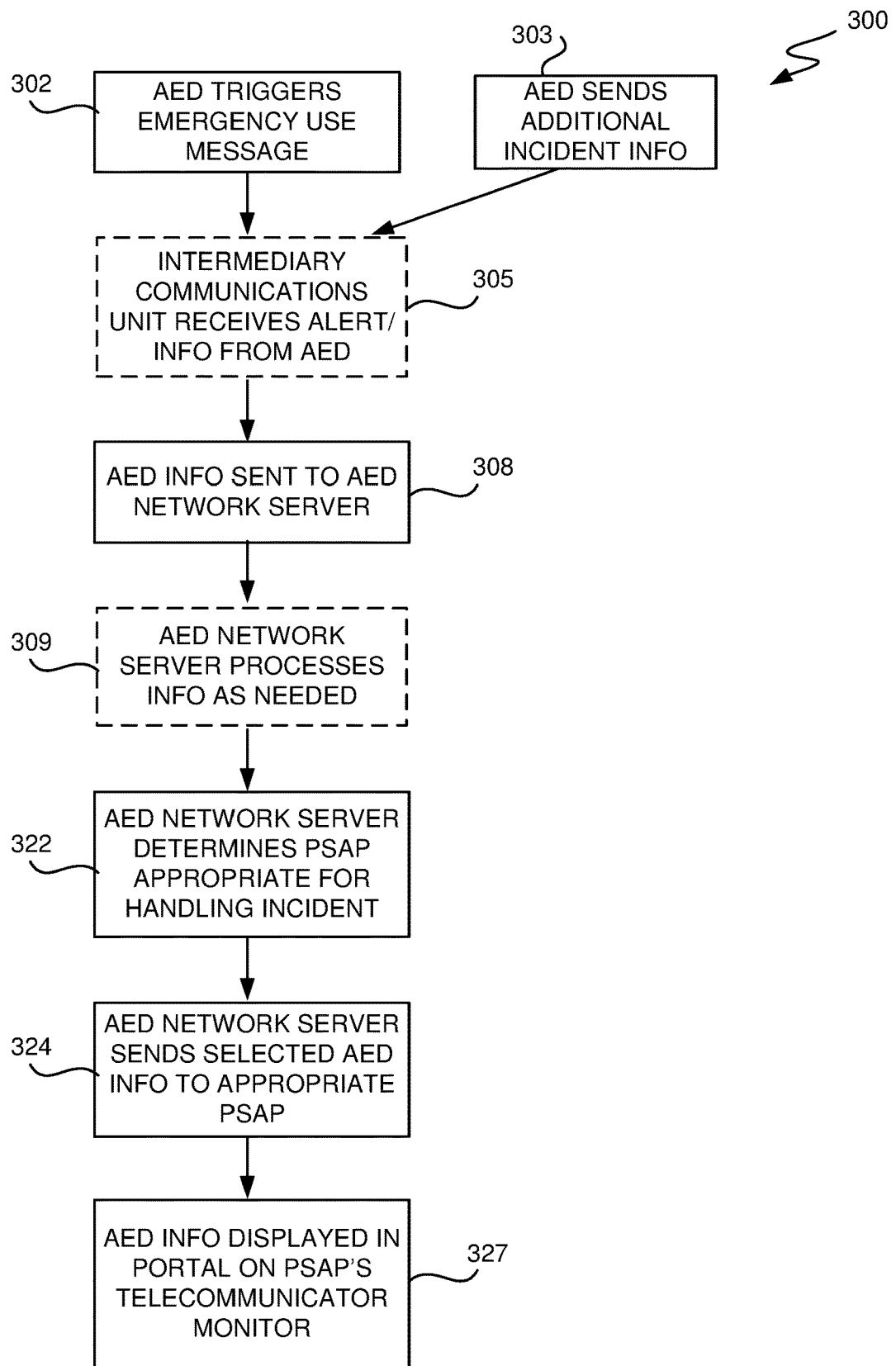

The method described with respect to FIG. 2A contemplates the use of a discrete ESI 28 that is distinct from AED network server 20 as illustrated in FIG. 1A. When the AED network server 20 itself functions as an ESI, the process can be simplified as illustrated in FIG. 2B. In this circumstance, the network server 20 determines the appropriate PSAP for handling the incident as represented by block 322. The network server 20 then forwards the AED info to the identified PSAP as represented by block 324. In other respects, the process of FIG. 2B may be similar to that described above with respect to FIG. 2A.

Figure 3A:
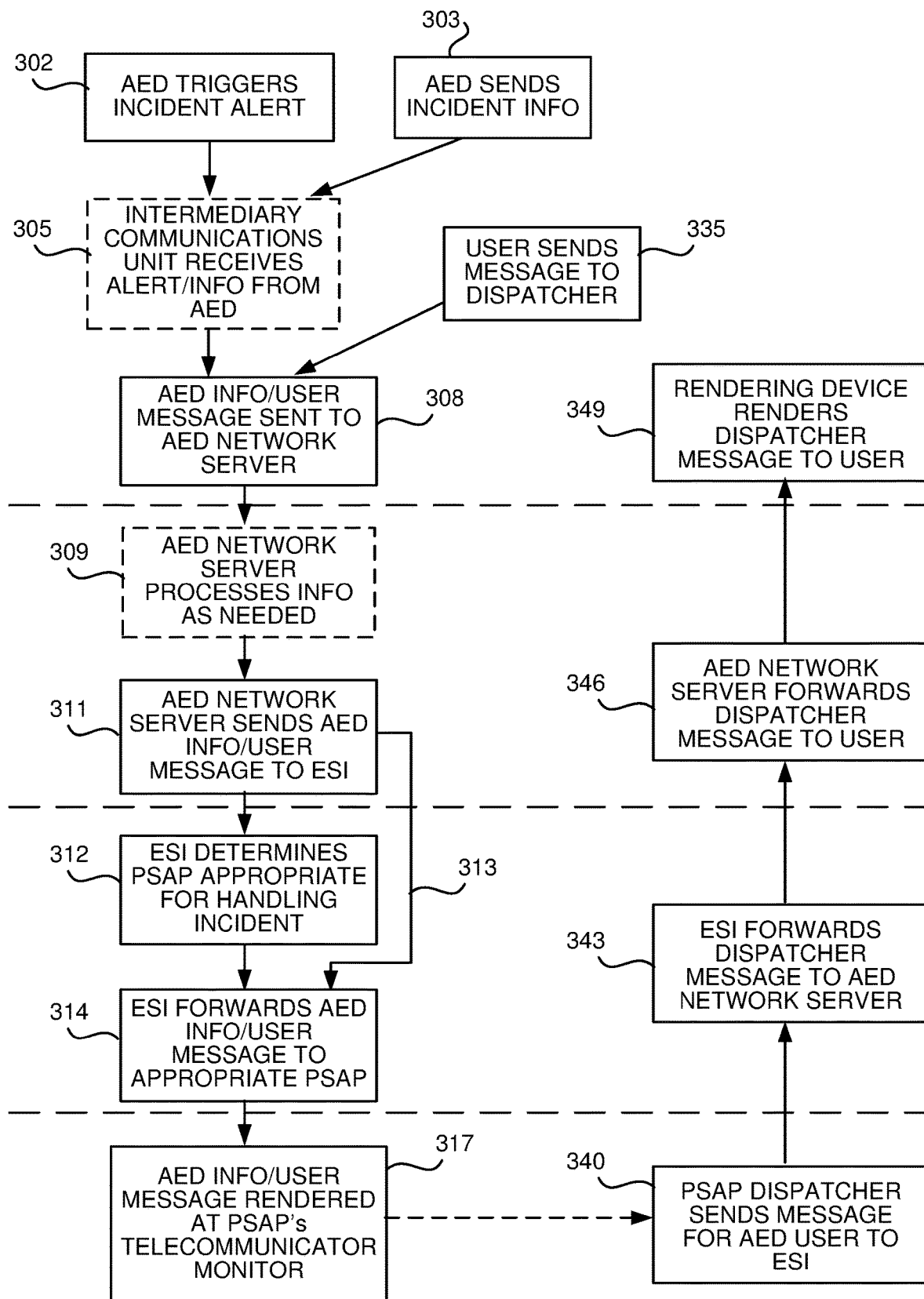
FIGS. 3A and 3B are flow charts illustrating two different approaches that facilitate bi-directional communications between a user of an AED and a telecommunicator at the PSAP.

There are times when it may be desirable to enable two way voice communications between an AED user and a PSAP telecommunicator through the AED itself (or a communications unit associated with the AED), rather than forcing the user to try to make a separate call to emergency services (e.g., 911) through their cell phone or relying on a bystander as an intermediary. If/when desired, such 2-way communications can readily be facilitated using substantially the same architecture and flow discussed above with respect to FIGS. 1A and 2A. One such flow is shown in FIG. 3A. In the illustrated embodiment, the initial connection and additional defibrillator data flow may be substantially the same as discussed above with respect to FIG. 2A and repeated in blocks 302-317 of FIG. 3A.

Upstream voice messages from the user (block 335) may be transported to the telecommunicator using the same path and rendered in real time at the telecommunicator's workstation (block 317). Conversely, downstream voice messages from the telecommunicator to the user may be delivered via the reverse path. That is, when the telecommunicator sends a voice message to a user, the message is first transmitted from the PSAP system 30 to the ESI 28 as represented by block 340. The ESI 28 then forwards the dispatcher message to the AED network server as represented by block 343. The AED network server then forwards the dispatcher message to the appropriate rendering device, as represented by block 346. The rendering device, which may be interface device 15, Smartphone 18, a suitable enabled AED 10(*a*) or other suitable device then plays the message to the user in real-time as represented by block 349. As will be apparent to those familiar with the voice messaging arts, a variety of readily available real-time voice messaging technologies can be used to facilitate such 2-way voice communications between the AED user and the PSAP telecommunicator over the defined path.

In the description above, 2-way voice communications has been described. However, it should be appreciated that textual, graphical imagery and/or other messages can be transmitted back and forth between the user (or a bystander) and dispatcher using the same approach. There are a wide variety of use cases for such messaging.

In some circumstances, the telecommunicator can send a message to the AED that causes the AED to generate a specific audio instruction. For example, an AED that has the capability of operating in either a normal (adult) or pediatric (child) mode may have an audio instruction something like: "if patient is a child under 8 years old, press the child button." The telecommunicator may know from a caller (or other source) or otherwise suspect that the patient is a child. In parallel, the telecommunicator may see that the AED is not in pediatric mode. In such circumstances, the dispatcher can send a 'trigger' message to the AED that causes the AED to generate the "if patient is a child under 8 years old, press the child button" instruction in response to the trigger. The AED can generate the triggered instruction at a convenient time in its workflow. In various embodiments, the triggered instruction can include audio and/or associated graphics to be displayed on a display screen. The triggered instruction(s) may be played or rendered by the AED itself, by an interface unit associated with the AED, and/or by a connected device as discussed in some of the incorporated patents.

Of course, there are many other examples of messages or instructions that may be triggered by the dispatcher. For example, if the dispatcher knows that an AED is present at the scene but has not been powered on, the dispatcher can send a trigger message that causes the AED or associated device to generate a "Turn me on" message to encourage user to activate the AED. In another example, if the dispatcher sees that pads have not been applied to the patient, appropriate pad placement instruction(s) may be triggered.

The triggered instruction may be the standard pad placement instruction or, if available, a more detailed pad placement instruction than is normally rendered by the AED.

In another example, if the dispatcher sees that the caregiver's CPR performance is dropping off, the dispatcher may send a trigger message to the AED that causes the AED to play or re-play an appropriate message or instruction. The specific message(s)/instruction(s) rendered may vary based on the capabilities of the AED. For example, the message may be a general instruction that encourages the user to push hard and deep, or more a more tailored instruction to push harder and deeper), or at a consistent rate, etc. that they dispatcher may trigger based on what performance criteria is dropping off.

Often, it will be desirable to constrain the instructions that are triggerable by the telecommunicator to a small set of pre-defined instructions that the AED is configured to handle in a specific predetermined ways. Such constraints can be particularly valuable from a security standpoint. The security if further enhanced by the described architecture in which the instructions are passed to the AED by way of the AED network server—which from the AED's perspective, is a known and trusted source. In some implementations, triggering instructions are only acted on by the AED if they are received via the AED network server.

Figure 3B:
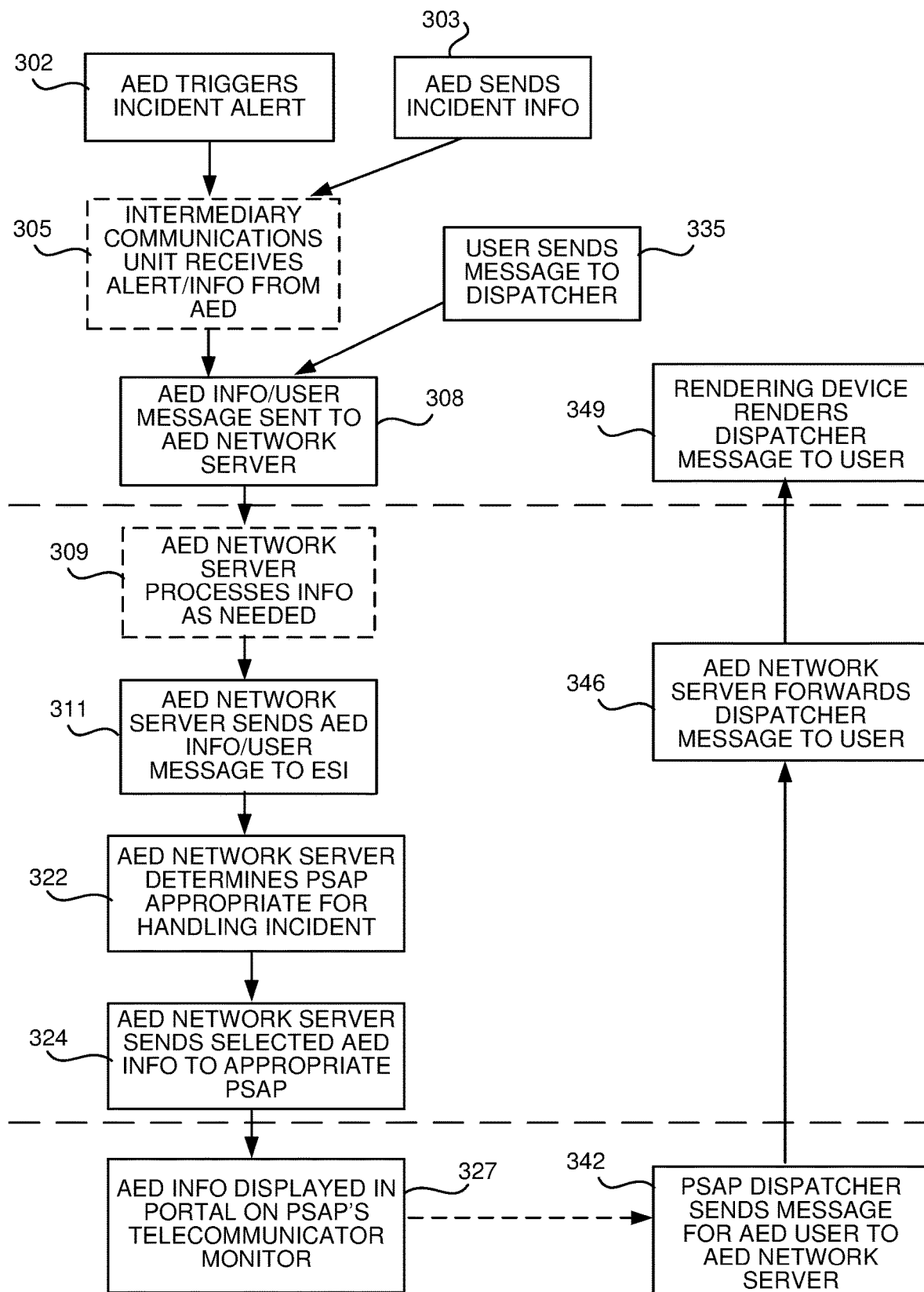

Like the method described in connection with FIG. 2A, the method of FIG. 3A contemplates the use of a discrete ESI 28 that is distinct from AED network server 20 as illustrated in FIG. 1A. When the AED network server 20 itself functions as an ESI, the process can be simplified as illustrated in FIG. 3B. In this circumstance, the PSAP 30 send messages for the AED user directly to the AED network server 20 as represented by block 342. In other respects, the flow of downstream communications from the PSAP to an AED may be similar to those described above with respect to FIG. 3A. The upstream communications may be similar to those described above with respect to FIG. 2B.

FIGS. 3A and 3B show downstream communications 340-349 in the context of 2-way communications. However, it should be appreciated that the same flow can be used to accommodate any downstream communications from a dispatcher to a user including dispatcher initiated communications regardless of whether 2-way communications are enabled.

Using the AED network server and optionally an emergency services interface as intermediaries in communications between the AED and emergency services has several advantages both in implementation ease and overall security. The security is enhanced because the AEDs are known as authenticated by the AED network server 20. When a separate ESI 28 is utilized, the AED network server 20 is known and trusted by the emergency services interface 28. The ESI 28 or the AED network server 20 when it also functions as an ESI, is known and trusted by the emergency call centers (PSAPs 30). From the perspective of the PSAP, any communications received from an AED are received from a trusted source (e.g., the AED network server 20 or the ESI 28), which can be white listed. Similarly, from the perspective of the distinct ESI 28, all data received over an IP connection from an AED are received from a trusted source (the AED response network server 20, which again can be white listed). In contrast, allowing call centers to accept connections from AEDs without going through the AED response network server would introduce a significant security risk to the call centers.

Furthermore, it is believed that the described approach is particularly easy to implement. This is in part due to the fact that existing emergency services interfaces 28 are already trusted data providers for many call centers, which significantly simplifies the AED network/call center integration process. It also leverages the benefits of AED networks which may be utilized independently for managing AEDs and other purposes. Furthermore, since PSAPs are currently accustomed to working with ESIs, the described framework is particularly easy to integrate with PSAPs even if the AED network server is designed to function as a "new" ESI.

It is noted that ESI's may be notified of potential emergency incidents from a number of different devices/sources well outside the realm of medical devices in general and AEDs in particular. Due to the risk of false alarms, most of the detected actions or events that trigger an API call to the ESI must be verified before a call is made or data is sent to a PSAP. Consider for example a security alarm system in which an alarm is triggered if a person entering a premise doesn't enter the correct PIN quickly enough to disable the alarm. In large part due to the risk of false alarms, most device triggers must be verified by a human before a voice call is made or data is sent to a PSAP. This is typically accomplished by a monitoring service. As such, when the ESI receives a device triggered alarm, the message is typically sent to a monitoring service that verifies that the alarm is a real emergency. If the incident was a false alarm, the ESI call is effectively ignored, and no voice call is made and no incident data is sent to a PSAP. In contrast, when the emergency is verified (using the protocols defined by the monitoring service), a voice call is typically made by the monitoring service to the appropriate PSAP to report the incident. In parallel, the ESI is informed that the incident has been verified which causes any appropriate device data to be forwarded to the appropriate PSAP.

When the AED server 20 determines that an AED is being used in an emergency incident (e.g., when it is determined that the AEDs electrode pads have been deployed), there is a high degree of confidence that the AED is being used in a real emergency that needs to be responded to. Therefore, in some embodiments, the API call from the AED network server 20 may be treated as a Verified Request. The Verified Request causes the ESI to immediately respond to the incident alert by transmitting any appropriate data directly to the PSAP. If desired, the ESI or the AED network can further employ a monitoring service (internal or external) that makes a parallel voice call to the PSAP to report the incident. In other embodiments, a monitoring service could be used to verify the defibrillator incident prior to forwarding the defibrillator data to the appropriate PSAP—although such an approach inherently slows the response time.

Figure 4:
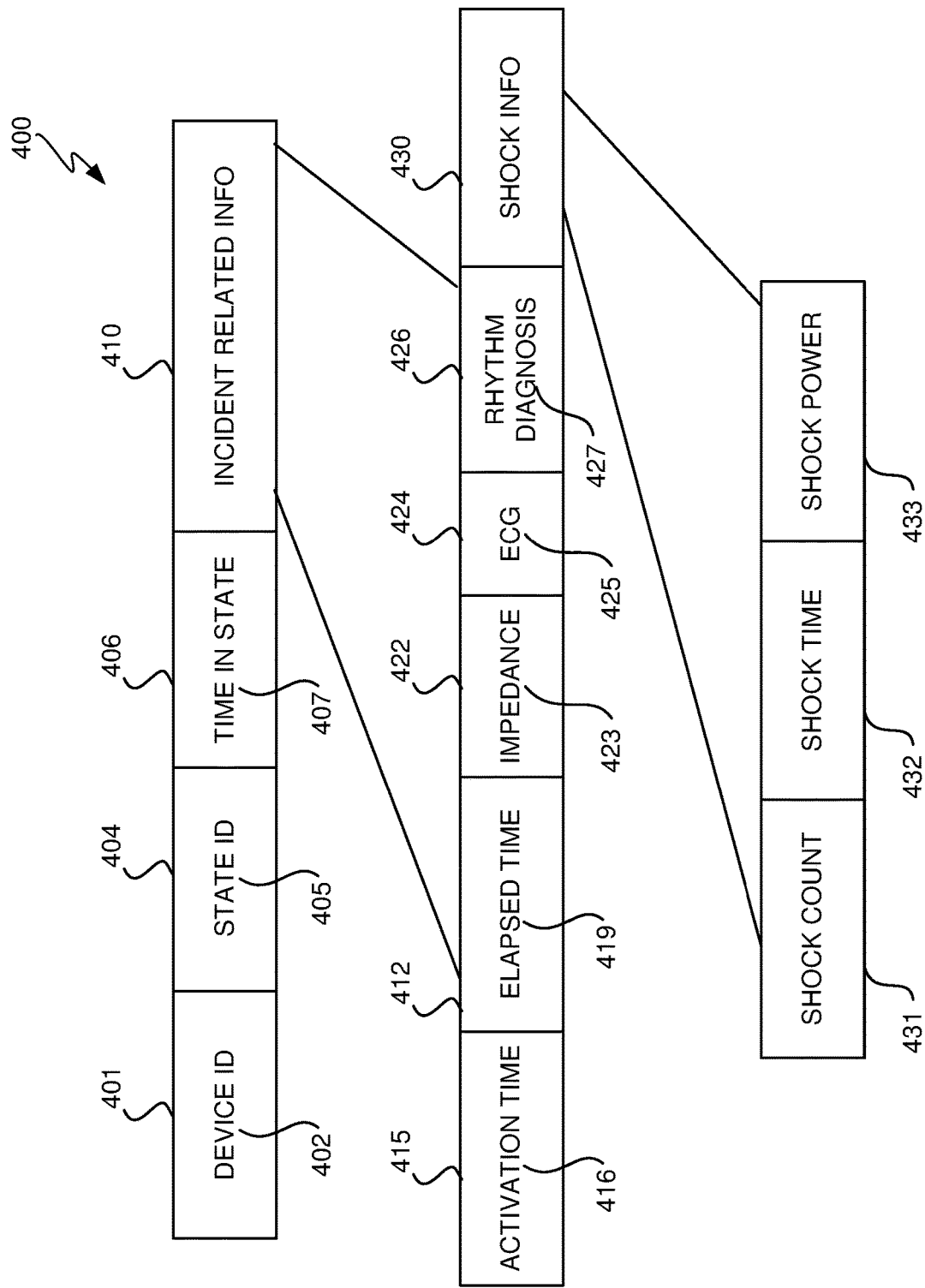
FIG. 4 is a block diagram illustrating a representative status message sent by an AED during emergency use of the AED.

In some embodiments, AEDs 10 are configured to periodically send incident status messages during emergency use of the AED. Such incident status messages may be passed on to the AED network server 20 and the information that is relevant to the PSAP can be forwarded on to the ESI 25 and PSAP 30 as appropriate. The format and content of the incident status messages may vary widely. By way of example, one suitable incident status message format is diagrammatically illustrated in FIG. 4. Others are described in the incorporated U.S. patent application Ser. Nos. 16/733, 591 and 16/733,684 and a variety of other message structures/contents may be utilized. In the embodiment illustrated in FIG. 4, the incident status message 400 includes: (1) an AED identifier field 401; (2) a state field 404; a time in state field 406; and (3) various incident related information 410.

The AED identifier field 401 may include a device identifier 402 that uniquely identifies the AED. In some embodiments this may take the form of a device serial number. The state field 404 includes a state identifier 405 that corresponds to the current event state of the AED. In some implementations each instruction that can be issued by the AED during emergency use of the defibrillator is assigned a unique state identifier. Thus, some of the available event states are instruction states. Therefore, any device that receives the incident status message 400 knows the AEDs current instruction state. The instructional state may be used by receiving devices such as interface unit 15, Smartphones 18 or other intermediary devices to facilitate the display of graphic instructions on the listening device that are synchronized with audio instructions issued by the AED. Such a system is sometimes referred to herein as "in sync graphics" and is described in detail in U.S. patent application Ser. No. 16/145,657 which is incorporated herein by reference. Although instruction states are an important set of the potential defibrillator states, it should be appreciated that the set of available states is not limited to instruction states. Rather, there may be any number of defibrillator states that are not associated with any particular instruction. The AED state information can also be utilized to inform the telecommunicator of the AEDs current state in real time.

The time in state field 406 includes a state timer 407 that indicates how long the AED has been in the current state identified by state identifier 405. As discussed above, the amount of time that the AED has been in any particular instruction state can provide useful information to the telecommunicator. For example, if the AED has been in a particular instruction state (e.g. apply the red electrode pad) for an extended period, that may suggest that the caregiver is stuck on that step and the telecommunicator can provide specific guidance that may be helpful to the caregiver based on the actions required given the state that the caregiver appears to be stuck on.

The incident related information that is conveyed as part of a incident status message 400 may vary widely as appropriate for any particular implementation. In general, any defibrillator related information that is perceived to be useful to any of the caregiver that is utilizing the AED, responding emergency medical technicians (EMTs) and/or the telecommunicator may be included in the incident status messages. In the embodiment illustrated in FIG. 4, the incident related information includes an activation time field 415, an elapsed time field 418, a detected impedance field 422, an ECG field 424, a rhythm diagnosis field 426 and a shock field 430. In other embodiments, more, fewer and/or different information fields may be provided.

The activation time field 415 includes an activation time identifier 416 that is effectively a timestamp of when the AED was activated. As mentioned above, in some implementations, the device identifier 402 and the activation time identifier 416 may be concatenated to create a unique Incident ID (UUID) that can be used to ensure that information transmitted to the network server 20, ESI 28 and PSAP 30 is always associated with the correct incident.

The time elapsed field 418 includes an elapsed time identifier 419 that indicates the amount of time that has elapsed since the AED was activated. In other embodiments, the time elapsed field may include a timestamp or equivalent indicating the current time so that a receiving device itself can determine the elapsed time and/or verify the order of received messages.

The impedance field 422 may include an indication of the most recent patient impedance detected by the AED, an impedance graph 423 showing variations in the detected impedance over time and/or any other desired indication of impedance detected by the AED. The detected impedance can be helpful in verifying whether the electrode pads have been placed on the patient and/or if out of the range of expected impedance may suggest that the pads have not been attached properly or have been placed wrong. The impedance graph can provide the telecommunicator with an indication of whether CPR is being performed (and/or performed at the right time).

ECG field 424 may provide a recently detected ECG segment 425 (e.g., the most recent ECG segment).

The rhythm diagnosis field 426 includes a rhythm identifier or diagnosis 427. In some embodiments that may take the form of a simple flag that indicates whether the cardiac rhythm detected is shockable or not. In others, the rhythm diagnosis may indicate the type of cardiac rhythm that has been identified by the AED's classifier (e.g., ventricular fibrillation (VF), ventricular tachycardia (VT), etc.). In some implementations multiple rhythm identifications can be provided. For example, it may be desirable to provide an original (pre-shock) rhythm diagnosis in addition to the current rhythm diagnosis. If multiple shocks have been delivered, it may be desirable to provide the original rhythm classification together with the diagnosis that was made after each administered shock including the current rhythm diagnosis (e.g., normal, VF, VT, etc.).

The shocks field 430 includes a shock count identifier 431 that indicates the number of shocks that have been delivered as part of the current incident. In some embodiments, the shock count identifier 431 may be followed by shock information that identifies the timing and nature of each delivered shock. The specific shock information provided may vary widely based on the design goals and needs of any particular systems. By way of example, in some embodiments, for each administered shock, a timestamp 432 and a power level indicator 433 provided. The timestamp 432 indicates the time that the shock was delivered. The power level indicator 433 indicates the nominal (or measured) energy delivered by the associated shock (e.g., 150 joules, 180 joules, etc.).

When CPR related feedback (e.g., compression rate, compression depth, etc.), the incident status messages may include such information as well (not shown). Such CPR related feedback can be useful to the telecommunicator to facilitate coaching the responder/caregiver to provide more effective CPR when appropriate. When the AED or a device associated therewith has the ability to analyze the quality of CPR compressions the status reports may include such information as well (e.g., an indication of the quality of compressions delivered, or the percentage of compressions were quality compression vs. not).

Although a few specific incident status message indicators have been shown, it should be appreciated that a variety of other indicators/fields may be provided as appropriate for any given implementations. For example, in some embodiments, a child/adult indicator is provided that indicates whether the AED is/was in a normal or pediatric operating mode. In some embodiments a language indicator is provided which indicates the language that instructions are being delivered in (e.g., English/Spanish, etc.) Of course, the specific information that is conveyed as part of an incident status message 400 may vary widely, with more, less or different information being transmitted as appropriate for any particular implementation.

When the AED is activated for emergency use, the AED transmits the incident status message 400 at regular intervals. The specific intervals used may vary but they are preferably fairly frequent. By way of example, frequencies on the order of one or more status messages per second works well (e.g., 0.5-20 Hz) for facilitating in-synch graphics and allows impedance variations to be tracked very closely. Although such frequencies work well for the purposes of T-CPR, it should be apparent that the messages can be transmitted and/or forwarded to the PSAP at lower or higher frequencies to meet the needs of T-CPR. In some specific implementations, incident status messages are sent at regular intervals (e.g., at a frequency of 1 Hz) and any time there is a change in audio instruction (or other) state.

There are a number of services that can be provided by software executing on one or more of the nodes to make the defibrillator information more presentable to the telecommunicator. For example, it may be useful for the telecommunicator's UI to include a timer that shows how long the AED has been in the current instruction state. If such information is not explicitly transmitted by the defibrillator, the time in current state can be determined at any of the nodes that receive the current instruction state (e.g., AED network server 20, ESI 28, etc.) and included in the incident information transmitted to the PSAP, or may be determined at the PSAP itself. The UI in the telecommunicator's ESI portal 52 may then include a field that identifies the current AED instruction state and a timer that indicates how long the AED has been in that state. It should be apparent that the AED server, and/or software executing at the PSAP or at any other node can readily tract the time from the point at which it first received a status report indicating that the AED is in a particular state (e.g. a particular instructions state, or that the pads are connected to a patient). Such "time in state" information can then be transmitted to the PSAP and/or rendered on the telecommunicator's display screen in conjunction with the associated state or instruction state.

In another example, a service may be provided to create a graph showing the detected impendence or ECG and its variations over time. For example, if the AED's status reports simply provide an indication of the most recently detected impedance, a service at the AED network server or any other suitable node can create a graph or set of impedance readings that shows impedance variations over time. Such time based impedance information can be transmitted to the PSAP and/or rendered on the telecommunicator's display screen. Similarly, services may be provided to combine ECG segments or any other information received from the AED and/or sensors in graphs or other suitable renderings that show variations in the detected parameters as a function of time.

Applicant has developed AED interface units that have the ability to receive real-time incident data from an AED during emergency use of the AED. The interface units are also able to communicate with external systems during emergency use of the AED as well as in non-emergency settings. Such communications may be made via Wi-Fi networks, cellular networks, and/or other suitable networks. By way of example, some representative interface units are described in U.S. patent application Ser. Nos. 16/145,657 and 16/146,096 and PCT Application No. PCT/US18/53321 which are all incorporated herein by reference. Other existing and proposed AEDs have incorporated or proposed various levels of communication capabilities or are configured to work with separate communication units that facilitate communications with remote servers. Applicant is also developing an AED that is capable of communicating with remote devices via other intermediaries, such as bystander's mobile communications devices (e.g., cellular smartphones) and/or other suitable configured nearby devices. By way of example, some such AEDs are described in U.S. patent application Ser. No. 16/733,591 and PCT Application No. PCT/US20/12146, which are also each incorporated by reference.

Still further, Applicant is developing responder networks which allow emergency services call centers to notify volunteer responders and AEDs of nearby potential cardiac arrest incidents and facilitate selected communications between AEDs and emergency call centers. In some implementations, communications between an AED and an emergency service call center is facilitated through intermediaries such as a responder network server and/or an emergency services interface such as RapidSOS. By way of example, some such responder networks are described in U.S. Patent Application Nos. 63/242,610 (P025P); Ser. Nos. 16/562,870 and 16/562,864 and PCT Application No. PCT/US19/49876, which are also all incorporated herein by reference.

The various incorporated patents and patent applications describe systems that can be used to communicate incident data detected by an AED to an appropriate emergency services call center (and/or other appropriate medical institutions/personnel) in real-time during emergency use of the AED. The present disclosure contemplates making selected AED incident information available to the telecommunicator that is handling the incident in real-time so that such information can be used to help the telecommunicator provide more effective T-CPR and/or AED use instructions to the caller. In different circumstances, the caller may be: (a) a bystander that is distinct from a volunteer responder/caregiver (user) that is using the AED and/or providing CPR; (b) the (or one of the) volunteer responder(s) using the AED and/or providing CPR; or (c) the call may be initiated by the AED itself, or by an interface or communications unit associated with the AED.

Data Transfers to Hospitals and EMS

It is also desirable to deliver defibrillator incident data to the medical personnel and/or medical facility(ies) that are responsible for treating the patient after the handoff from EMS. Such data can be delivered in a number of different ways. In some embodiments, the emergency call center can forward defibrillator incident data to the responding EMS unit. If available and desired, the EMS can view such data on the way to an incident so that they have a better understanding of situation before they arrive at the scene. Even when EMS does not itself review the incident data (which may often be the case), it can still provide a mechanism for delivering the incident data to the patient's medical records.

Specifically, when a patient is taken by EMS to a medical facility such as hospital, the EMS responder will typically deliver an incident record to the medical facility. Sending the defibrillator incident data to EMS via the emergency call center allows the EMS unit to include the defibrillator incident data in the incident record provided to the medical facility, which in turn can enter such data into the patient's medical records.

In other embodiments, the defibrillator incident data can be provided to the appropriate medical facility(ies) directly (or indirectly) from a defibrillator management server that receives the incident data directly from the defibrillator. In some implementations, the management server may integrate with medical records/medical facilities through an Electronic Patient Care Reporting (ePCR) service. It should be appreciated that in some embodiments, the defibrillator incident data will be sent from the AED to the defibrillator management server during emergency use of the AED—which forwards such information to the responsible emergency call center either directly or through an emergency services interface as discussed above, so the defibrillator management server may already have the defibrillator incident data available to forward to medical facilities/personnel as appropriate.

Additionally, or alternatively, the defibrillator may create an incident log during emergency use that contains all data from the incident that is considered important. The incident log may then be transmitted to, retrieved by, or otherwise conveyed to an incident report server and/or an ePCR service—which makes the reports available to appropriate medical and/or emergency services personnel, and/or integrates the incident log with the patient's record. By way of example, U.S. Patent Application No. 63/004,320 and Ser. No. 17/217,738 (P022), which are incorporated herein by reference, describes some specific ways of making incident logs available to medical personnel. There is a variety of defibrillator based information that may be of interest to medical personnel that is not available from other sources. Any or all of such information can be included in the defibrillator incident record provided by the defibrillator. This may include information such as the ECG rhythms detected by the defibrillator, AED use related information, various information about the shock decisions and any shocks that are delivered, CPR related feedback, etc.

With respect to the ECG rhythms, one rhythm of particular interest is the initial rhythm detected by the AED. The true initial rhythm can be a very important piece of information for electrophysiologists when they are deciding a care plan for the patient and are not conventionally available since the presenting rhythm when EMS arrives is often different than the initial rhythm that the patient experienced, especially when a defibrillator has been used. Various other ECG segments are also of interest. In some embodiments, the defibrillator incident record includes all ECG segments detected by the defibrillator while the electrode pads are coupled to the patient. In other embodiments selected ECG strips are presented—as for example, the initial segment, each segment used in a shock/no shock determination, and the rhythms detected after each shock delivery.

The AED use related information may include information such as the time from AED activation to incident end, etc.

Shock related information may include the number of shocks delivered (if any), the time that each shock was delivered (relative to AED activation) and the energy level imparted by the shock. It may also include the results of each shock/no shock decision and the relative timing of such decisions.

In some embodiments, the incident report may include an annotated timeline that identifies the timing of various events of significance—e.g., CPR started (or CPR instruction given), shockable rhythm detected, shock delivered, normal rhythm detected, etc.

CPR related feedback may include feedback such as compression rates, compression depths, the quality of compressions delivered, what percentage of compressions were quality vs. not, the percentage of time that CPR was actually performed when it was supposed to, vs. not, etc.

Of course, the defibrillator incident record delivered to the medical facility may include any other information available to the defibrillator that is deemed of interest to medical personnel. For example, in some devices associated with a patient may have medical related information that may be useful to attending medical personnel. For example, a health app on a victim's Smartphone or an EKG monitoring product such as the AliveCor KardiaMobile may have information about the patient's health immediately preceding a cardiac arrest incident, e.g., ECGs, heart rate, blood pressure, blood oxygen levels, etc., which may be useful to medical personnel. In some implementations, the AED may be designed to query such devices associated with the patient and to add relevant information from such devices to the incident report.

Other Features

Although only a few embodiments of the invention have been described in detail, it should be appreciated that the invention may be implemented in many other forms without departing from the spirit or scope of the invention. In the foregoing specification, several specific types of AED incident information that can be particularly useful for telecommunicators when guiding volunteer caregivers through the use of an AED and/or CPR have been described. One such example is the AEDs current instruction state which can be particularly useful for providing the telecommunicator with an understanding of where the caregiver is in the process. Another example is providing an indication of the time that the AED has been in a particular state (e.g., a particular instruction state, or more generally a particular AED state)— which may provide clues as to when a caregiver is stuck on that step. The detected patient impedance or an impedance graph can also provide a variety of useful be useful information as to the likely current state of the defibrillators use (e.g. whether the electrode pads have been place properly or feedback illustrative of whether CPR is being performed).

In some of the embodiments described above, communications between the AED and the PSAP pass through AED both network server 20 and ESI 28. In alternative implementations, one or both of these intermediaries can potentially be eliminated. For example, AEDs (or communication units associated therewith) could directly contact ESI 28 or AED network server 20 could be arranged to communicate directly with the PSAP.

Further, if desired, the novel types of AED incident information delivered to a PSAP for facilitating T-CPR (which as used herein encompasses AED use guidance) can be delivered directly from an AED (or a communications unit associated therewith) to a PSAP if/when the PSAP is designed to directly accept data calls. Of course, such AED incident information can be delivered to the PSAP via any other suitable means as well.

Much of the discussion above refers to communications between an AED and an AED network server. Some AEDs will have an integrated communications unit so that communications can be made directly with the AED. However, in many other applications, the AED itself will not have a communications unit that is suitable for communicating with the AED network sever. Rather, a separate interface unit or communications unit may be provided that has such abilities. In some circumstances, the interface unit may be a separate unit that is physically attached to a fully functional AED such that it can be (and is intended to be) carried together with the AED as a single unit even though it is architected as a modular system. In such circumstances, the AED (which might be considered a base defibrillator unit) may be a fully functional defibrillator that is capable of (and/or designed to) operate independently with or without the presence of the interface unit. In such circumstances the communications with the AED network server may be with the independent interface unit or communication unit rather than the base defibrillator unit itself. A good example of such a modular system is described in the incorporated U.S. Pat. Nos. 10,773,091 and 10,737,105. However, for the purposes of this disclosure and claims, communications with such systems is contemplated to be within the scope of the described communications with an AED unless the context precludes such interpretation. Communications between the various nodes in the system can be made using any suitable communications protocol.

Several of the workflows described above were described at least in part through the use of flow charts which suggest a particular order of steps. In some circumstances the order of events may be important as suggested by the context. However, in others various steps may be reordered or eliminated and other steps may be added without departing from the spirit and scope of the invention.

The inventions have been described primarily in the context of telecommunicator providing guidance to callers in circumstances in which a volunteer responders/caregiver is utilizing an AED while responding to cardiac arrest incidents. However, it should be appreciated that a similar approaches and systems can be used in conjunction with telecommunicator guidance involving the use of other types of connected medical instruments, devices or kits (as for example a connected first aid kit or a connected EpiPen). Therefore, the present embodiments should be considered illustrative and not restrictive, and the invention is not to be limited to the details given herein but may be modified within the scope and equivalents of the appended claims.

The invention claimed is:

1. A method of communicating defibrillator incident information to a telecommunicator at a Public Safety Answering Point (PSAP) in real time during emergency use of an automated external defibrillator (AED), the method comprising:
   at an AED network server, receiving defibrillator incident information generated by the AED directly or indirectly from the AED in real time during the emergency use of the AED; and
   electronically transmitting at least selected portions of the defibrillator incident information from the AED network server directly or indirectly to the PSAP, the PSAP being located remotely relative to the AED network server and being responsible for handling calls to emergency services originating from an area that includes a current location of the AED, wherein the selected defibrillator incident information is forwarded to the PSAP in real time during the emergency use of the AED such that the selected defibrillator incident information can be utilized in real time by the telecommunicator to provide directions to a caregiver utilizing the AED or a caller at the location of the AED during the emergency use of the AED.

2. A method as recited in claim 1 wherein the AED network server processes at least some of the defibrillator incident information received from the AED and at least some of the selected defibrillator incident information transmitted to the PSAP is transmitted in a different format than such defibrillator incident information was received in.

3. A method as recited in claim 1 further comprising displaying at least some of the selected defibrillator incident information on a display at the PSAP for use by the telecommunicator in real time while communicating with the caregiver or caller.

4. A method as recited in claim 3 further comprising the telecommunicator utilizing the selected defibrillator incident information to provide directions to the caregiver or caller during the emergency use of the AED.

5. A method as recited in claim 1 further comprising, at the AED network server, determining the appropriate PSAP to forward the selected defibrillator incident information to based at least in part on the current location of the AED.

6. A method as recited in claim 1 wherein the AED network server forwards the selected defibrillator incident information to an emergency services interface, the method further comprising, at the emergency services interface, determining the appropriate PSAP to forward the selected defibrillator incident information to based at least in part on the current location of the AED.

7. A method as recited in claim 1 wherein the selected defibrillator incident information includes a current user instruction state of the AED.

8. A method as recited in claim 7 wherein the selected defibrillator incident information further includes an indication of an amount of time that the AED has been in the current user instruction state.

9. An automated external defibrillator (AED) configured to electronically transmit selected defibrillator incident information directly or indirectly to a Public Safety Answering Point (PSAP) responsible for handling calls to emergency services originating from an area that includes a current location of the AED, wherein the selected defibrillator incident information is forwarded to the PSAP in real time during the emergency use of the AED such that the selected defibrillator incident information can be utilized in real time by a telecommunicator at the PSAP to provide directions to a caregiver utilizing the AED or to a caller at the location of the AED during the emergency use of the AED, wherein the selected defibrillator incident information includes at least one of a current or a next instruction state of the AED.

10. An AED as recited in claim 9 configured to transmit the defibrillator incident information to the PSAP via at least an AED network server.

11. An AED as recited in claim 9 configured to transmit the defibrillator incident information to the PSAP via at least an emergency services interface (ESI).

12. A method comprising:
    at an AED network server, directly or indirectly electronically receiving a message from a telecommunicator at a Public Safety Answering Point (PSAP), the AED network server being located remotely relative to the PSAP; and
    forwarding the message, or transmitting at least a portion of the information contained in the message, directly or indirectly to an automated external defibrillator (AED) to thereby facilitate communications from the PSAP to the AED via the AED network server.

13. A method as recited in claim 12 wherein the message is conveyed from the telecommunicator to the AED during emergency use of the AED.

14. A method as recited in claim 12 wherein the message is a triggering message that causes the AED to generate a predetermined audio instruction that is prestored by the AED.

15. A method as recited in claim 14 wherein the triggering message causes the AED to play or replay a CPR guidance instruction.

16. A method as recited in claim 14 wherein the triggering message causes the AED to play or replay an instruction that requests a user to select an operating mode appropriate for a patient that the AED is being used for.

17. A method as recited in claim 14 wherein the triggering message causes the AED or a unit associated with the AED to play an audio request to turn the AED on.

18. An AED network server configured to perform the method of claim 12.

19. A method of communicating information to a telecommunicator at a Public Safety Answering Point (PSAP), the method comprising:
- at an emergency services interface (ESI), receiving defibrillator incident information generated by and automated external defibrillator (AED) directly or indirectly from the AED in real time during the emergency use of the AED; and
- electronically transmitting at least selected portions of the defibrillator incident information from the emergency services interface directly or indirectly to the PSAP, the PSAP being located remotely relative to the ESI and being responsible for handling calls to emergency services originating from an area that includes a current location of the AED, wherein the selected defibrillator incident information is forwarded to the PSAP in real time during the emergency use of the AED such that the selected defibrillator incident information can be utilized in real time by the telecommunicator to provide directions to a caregiver utilizing the AED or a caller at the location of the AED during the emergency use of the AED.

20. A method as recited in claim 19 wherein the emergency services interface processes at least some of the defibrillator incident information received from the AED and at least some of the selected defibrillator incident information transmitted to the PSAP is transmitted in a different format than such defibrillator incident information was received in.

21. A method as recited in claim 19 further comprising displaying at least some of the selected defibrillator incident information on a display at the PSAP for use by the telecommunicator in real time while communicating with the caregiver or caller.

22. A method as recited in claim 21 further comprising the telecommunicator utilizing the selected defibrillator incident information to provide directions to the caregiver or caller during the emergency use of the AED.

23. A method as recited in claim 19 wherein the selected defibrillator incident information includes a current instruction state of the AED.

* * * * *